(12) United States Patent
Xiang et al.

(10) Patent No.: US 8,633,168 B2
(45) Date of Patent: Jan. 21, 2014

(54) INHIBITORS OF S-ADENOSYL-L-METHIONINE DECARBOXYLASE

(75) Inventors: Yibin Xiang, Waltham, MA (US); Bradford Hirth, Waltham, MA (US); Cassandra Celatka, Waltham, MA (US)

(73) Assignee: Genzyme Corporation, Cambridge, MA (US)

( * ) Notice: Subject to any disclaimer, the term of this patent is extended or adjusted under 35 U.S.C. 154(b) by 410 days.

(21) Appl. No.: 12/664,628

(22) PCT Filed: Jun. 13, 2008

(86) PCT No.: PCT/US2008/067028
§ 371 (c)(1),
(2), (4) Date: Jun. 16, 2010

(87) PCT Pub. No.: WO2008/157438
PCT Pub. Date: Dec. 24, 2008

(65) Prior Publication Data
US 2010/0261668 A1    Oct. 14, 2010

Related U.S. Application Data

(60) Provisional application No. 60/944,430, filed on Jun. 15, 2007, provisional application No. 60/956,921, filed on Aug. 20, 2007.

(51) Int. Cl.
*A61K 31/70*    (2006.01)
*C07H 19/00*    (2006.01)

(52) U.S. Cl.
USPC .......................................... 514/43; 536/22.1

(58) Field of Classification Search
USPC .......................................... 536/22.1; 514/43
See application file for complete search history.

(56) References Cited

U.S. PATENT DOCUMENTS 5,416,076 A    5/1995    Casara et al.
5,872,104 A    2/1999    Vermeulen et al.

FOREIGN PATENT DOCUMENTS

EP    0 472 181    2/1992

OTHER PUBLICATIONS

Marasco et al., J. Med. Chem., 2002, 45, 5112-5122.*
Bacchi et al., Antimicrobial Agents and Chemotherapy (1992) 36:2736.
Bacchi et al., Antimicrobial Agents and Chemotherapy (1996) 40(6):1448-53.
Beswick et al., Biochemistry (2006) 45(25):7797-7807.
Bitoni et al., Antimicrob. Agents Chemother. (1990) 34:1485-1490.
Bitoni et al., Biochem. J. (1991) 174:527.
Casara et al., J. Am. Chem. Soc. (1989) 111:9111.
Hirota et al., J. Org. Chem. (1992) 57:5268.
Hirumi et al., J. Parasitol. (1989) 75:985-989.
International Search Report for PCT/US08/67028, mailed on Sep. 8, 2008, 2 pages.
International Preliminary Report on Patentability for PCT/US08/67028, issued Dec. 17, 2009, 5 pages.
Jennings et al., Contrib. Microbiol. Immunol. (1983) 7:147-154.
Kawasaki et al., J. Med. Chem. (1993) 36:831-841.
Kinch et al., Mol. Biochem. Parasitol. (1999) 101:1-11.
Pankiewicz et al., J. Org. Chem. (1992) 57:553.
Robins et al., Can. J. Chem. (1991) 69:1468.
Willert et al., PNAS USA (2007) 104:8275-8280.

* cited by examiner

*Primary Examiner* — Elli Peselev
(74) *Attorney, Agent, or Firm* — Morrison & Foerster LLP

(57) ABSTRACT

Novel mechanism-based inhibitors of S-adenosyl-L-methionine decarboxylase are provided. These compounds of formula (1) inhibit the life cycle of trypanosomes, and are useful to treat subjects infected with African trypanosomes. The invention includes pharmaceutical compositions and methods of using the compounds of formula (1).

18 Claims, 6 Drawing Sheets

FIG. 1 (Prior Art) The structure of a representative compound and some of its biological and pharmacological data from the literature FIG. 2 (Prior Art) Mechanism of decarboxylation of AdoMet catalyzed by SAM DC (reference 17)

Mechanism of deactivation of SAM DC by a representative compound.

INHIBITORS OF S-ADENOSYL-L-METHIONINE DECARBOXYLASE

CROSS-REFERENCE TO RELATED APPLICATIONS

This application is the national phase of PCT application PCT/US2008/067028 having an international filing date of Jun. 13, 2008, which claims priority from U.S. Ser. No. 60/956,921 filed Aug. 20, 2007 and U.S. Ser. No. 60/944,430 filed Jun. 15, 2007. The contents of these documents are incorporated herein by reference.

TECHNICAL FIELD

This invention relates to novel inhibitors of S-adenosyl L-methionine decarboxylase (SAMDC) that kill or inhibit growth of trypanosomes, and to methods of using these inhibitors to treat disease conditions associated with trypanosomes and other diseases which may be treated by inhibiting polyamine synthesis.

BACKGROUND ART

Trypanosomes are parasites that cause a number of important diseases that are widespread in developing countries, including African sleeping sickness or trypanosomiasis. S-adenosyl-L-methionine decarboxylase (SAMDC) is a crucial enzyme in the biosynthesis of certain polyamines, such as spermidine and spermine. Inhibition of the production of these polyamines is detrimental to the survival and life cycle of certain microorganisms, including trypanosomes, thus inhibitors of SAMDC are useful to treat disorders such as trypanosomiasis.

Trypanosomiasis remains prevalent throughout sub-Saharan Africa, and includes both acute and chronic stages, and is caused by either of two trypanosomes, *T. brucei gambiense* and *T. brucei rhodesiense*. The chronic stage occurs where the trypanosome has invaded the CNS. It has been shown that inhibitors of polyamine biosynthesis, including ornithine decarboxylase inhibitors such as eflornithine (difluoromethyl ornithine), can inhibit growth of trypanosomes, and there is evidence that inhibitors of S-adenosylmethionine decarboxylase can also control trypanosome growth. C. J. Bacchi, et al., *Antimicrobial Agents and Chemotherapy*, 40 (6), 1448-53 (1996).

One known inhibitor of SAMDC is shown in FIG. 1: it is a mechanism-based inhibitor that irreversibly inhibits the enzyme. SAMDC decarboxylates SAM by the mechanism depicted in FIG. 2; inhibition of SAMDC by this compound is believed to operate by the mechanism depicted in FIG. 3. However, it has limited in vivo activity, which is believed to be due to rapid clearance and poor ability to cross the blood-brain barrier. The compound shows effective antitrypanosomal activity in cell based assays and in non-CNS trypanosome-infected mice models (FIG. 1). The compound, however, is not an ideal drug candidate because of its non-optimal pharmacokinetic profile and poor brain blood barrier penetration.

Other anti-trypanosome drugs are also known, including pentamidine, suramin, melarsoprol, eflornithine, and nifurtimox. However, all of these suffer from certain limitations, such as toxicity, complicated dosing regimens, susceptibility to resistance, lack of complete selectivity for enzymes in trypanosomes, poor pharmacokinetics, and poor transport across the blood-brain barrier to attack the CNS-active stage of trypanosomiasis. Therefore, there is a need for improved drugs to treat trypanosome infections, and for inhibitors of SAMDC that have increased bioavailability and ability to penetrate the blood-brain barrier. It has now been found that certain compounds of formula described herein inhibit SAMDC, and also inhibit trypanosome proliferation in vitro in a cell-based assay system. Without being bound by theory, it is believed that the inhibitors are mechanism-based inhibitors of SAMDC, and that their anti-trypanosomal activity is due to inhibition of SAMDC. These compounds exhibit improved pharmacokinetics, so their in vitro activity translates more efficiently into in vivo biological activity.

DISCLOSURE OF THE INVENTION

The present invention provides compounds of formula (1) and their pharmaceutically acceptable salts,

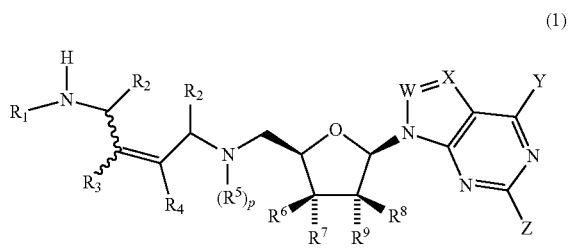

(1)

wherein:
W is N or $CR^{10}$;
X is N or $CR^{10}$;
Y is $NHR^1$; and
Z is H, $NHR^1$, F, Cl, $OR^1$, $CF_3$, or optionally substituted alkyl;
$R^1$ is selected from H, and optionally substituted acyl, alkyl, alkenyl, alkynyl, cycloalkyl, heterocyclyl, aryl, heteroaryl, and alkoxyacyl;
$R^2$ is, independently at each occurrence, H, substituted or unsubstituted acyl, or substituted or unsubstituted alkyl;
$R^3$ and $R^4$ are each independently H, F, Cl, CN, or COOR, where R is H or C1-C8 alkyl; or $R^3$ and $R^4$ taken together form a bond;
$R^5$ is H, or optionally substituted acyl, alkyl, alkenyl or alkynyl, or substituted or unsubstituted amino, substituted or unsubstituted alkoxy, or substituted or unsubstituted alkoxyacyl,
$R^6$, $R^7$, $R^8$, and $R^9$ are each independently H, OH, F, substituted or unsubstituted acyloxy, substituted or unsubstituted alkoxy, or substituted or unsubstituted alkyl, provided that $R^7$ and $R^9$ are not both OH when W is CH, X is N, and Z is H; and
$R^{10}$ is, independently at each occurrence, H, or optionally substituted alkyl, alkenyl, alkynyl, or acyl, or it can be halo, CN, or $CF_3$;
and p is 1 or 2.

In another aspect, the invention provides a method to treat an infection caused by a trypanosome: the method includes administering an effective amount of a compound of formula (1) as described above to a subject having a trypanosomal infection.

In another aspect, the invention provides a method to kill or deter growth of trypanosomes by contacting the trypanosomes with a compound of formula (1).

In yet another aspect, the invention provides a method to treat a disease or disease condition which is responsive to inhibition of polyamine synthesis by administering to a human or other mammal an effective amount of a compound of formula (1). Such diseases include hyperproliferative disorders including cancer and psoriasis, ocular proliferative disorders including macular degeneration and diabetic retinopathy, vascular restenosis and viral infections including HIV.

In formula (1), each $R^1$ is selected independently. Each $R^1$ can be H, or an optionally substituted alkyl, acyl, alkenyl, alkynyl, aryl, heteroaryl, cycloalkyl, heterocycloalkyl, or alkoxyacyl group. $R^1$ shown in formula (1) is preferably H or an acyl group; in certain embodiments it is H. Where $R^1$ is an acyl group, it can be unsubstituted, such as a formyl or acetyl group; or its alkyl portion can be substituted. Examples include methoxyacetyl, trifluoroacetyl, and alpha-aminoacetyl groups derived from amino acids such as the essential amino acids, i.e., $R^1$ can represent an amide of an alpha-amino acid such as glycine, alanine, leucine, valine, isoleucine, serine, or threonine. In other embodiments, the $R^1$ shown in formula (1) is alkoxyalkyl, such as methoxymethyl or methoxyethyl.

Each $R^2$ can be H or an optionally substituted alkyl or acyl group. In some embodiments, each $R^2$ is H. In other embodiments, each $R^2$ is H or C1-C4 alkyl.

$R^5$ can be H, or optionally substituted alkyl, amino, alkoxy, alkoxyacyl, or acyl, and in many embodiments it is C1-C4 alkyl, which can be substituted. In formula (1), p can be 1 or 2. In some embodiments, p is 1, so a single $R^5$ is present. Often in such embodiments, $R^5$ is methyl. Where $R^5$ is amino, it can be substituted or unsubstituted. In some embodiments, p is 2, so there are two $R^5$ groups present. In such embodiments, the nitrogen attached to $R^5$ is quaternary, and therefore that nitrogen atom has a positive charge, i.e., it is an ammonium nitrogen. In such embodiments, at least one $R^5$ is typically methyl. When p is 2, the two $R^5$ groups present can be the same or different. In some embodiments, one of the two $R^5$ groups is H, and the other is optionally substituted alkyl. In other embodiments, where p is 2, each $R^5$ is methyl.

$R^3$ and $R^4$ can be H, or fluoro, or optionally substituted alkyl, and in some embodiments, one of $R^3$ and $R^4$ is CN or an acyl group or COOR, where R is H or C1-C8 alkyl. Typically, $R^4$ is H or CN. In certain embodiments, each of $R^3$ and $R^4$ is H. In many embodiments, $R^3$ and $R^4$ are in a cis relationship on the depicted double bond. In other embodiments, $R^3$ and $R^4$ can be taken together to form a bond, so that the bond connecting the carbon atoms to which $R^3$ and $R^4$ are connected is a triple bond instead of a double bond.

$R^6$, $R^7$, $R^8$ and $R^9$ can be independently selected from H, OH, substituted or unsubstituted acyloxy, substituted or unsubstituted alkoxy, and substituted or unsubstituted alkyl; preferably $R^6$ and $R^8$ independently represent H or F. Frequently, at least one of $R^7$ and $R^8$ represents OH or acyloxy or alkoxy. The acyloxy group is often a hydroxyl acylated with a simple acyl group such as formyl, acetyl, or methoxyacetyl; or it is acylated with the acyl portion of an amino acid, such as valine, leucine, glycine, alanine, isoleucine, and the like. In other embodiments, at least one of $R^6$, $R^7$, $R^8$ and $R^9$ is F. Specifically preferred embodiments include those where $R^6$ and/or $R^7$ is hydroxyl or acyloxy. Suitable acyloxy groups include acetoxy, methoxyacetoxy, and C1-C6 acyloxy groups optionally substituted with amino or substituted amino.

W and X independently represent N or $CR^{10}$, where $R^{10}$ is H or halo, or optionally substituted alkyl, alkenyl, or alkynyl. In preferred embodiments, at least one of W and X is N. Where W or X represents $CR^{10}$, this $R^{10}$ is often H or F or Cl or Me or $CF_3$. In some embodiments, when X is N, W is $CR^{10}$, where $R^{10}$ is not H; preferably, $R^{10}$ is Cl, Me or $CF_3$.

Y represents $NHR^1$, where $R^1$ is as described above. In many embodiments, Y is $NH_2$. However, Y in some embodiments is $NHR^1$, where $R^1$ is a substituted or unsubstituted acyl group, such as formyl, acetyl, trifluoroacetyl, or an acyl group derived from an alpha-amino acid such as glycine, alanine, leucine, isoleucine, valine, serine, threonine or methionine.

Z is H, halo, optionally substituted alkyl (including $CF_3$), $OR^1$, or $NHR^1$, where $R^1$ is as described for $R^1$ on Y. Typically, Z is H, F or Cl; or it represents methyl or $CF_3$.

In some embodiments, $R^3$ and $R^4$ are in the cis or Z relative configuration.

Particular embodiments of the invention include these compounds, and the E-isomer of each of these compounds:

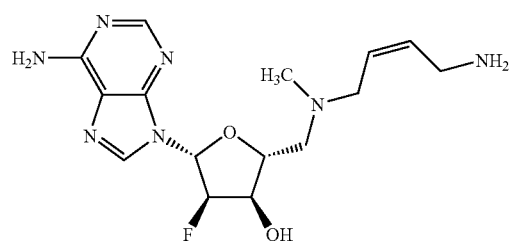

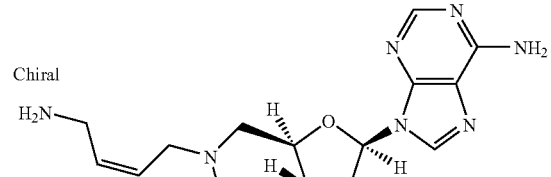

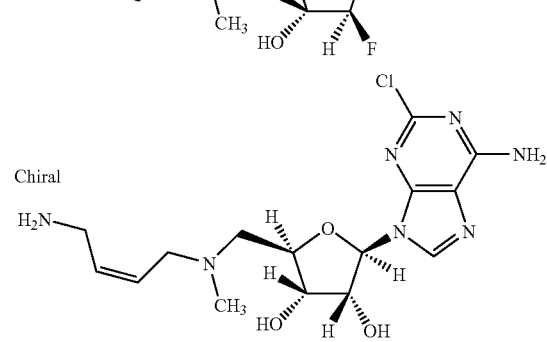

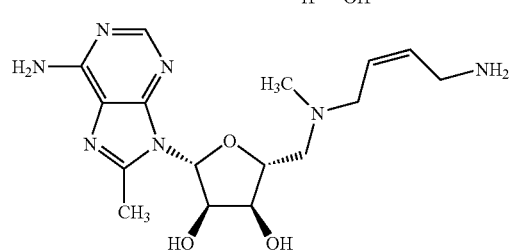

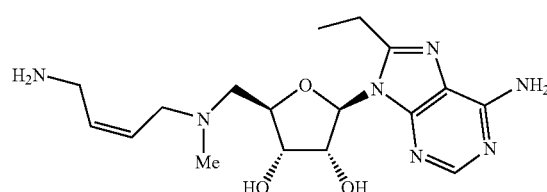

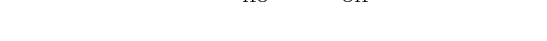

-continued

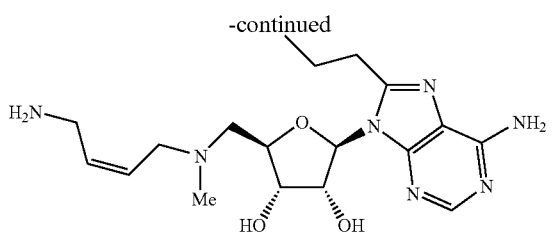

and derivatives of any of these compounds having one or more of their free amine or hydroxyl groups acylated with an optionally substituted acyl group. Typical acyl groups in such derivatives include formyl, acetyl, propionyl, and butanoyl, and amine-substituted acyl groups such as those derived from any of the essential amino acids, such as glycine, alanine, leucine, isoleucine, threonine, valine, serine, and methionine, for example. Particular embodiments include derivatives of these compounds that are acylated on at least one hydroxyl on the tetrahydrofuran ring, often with a C1-C4 acyl group such as acetate.

MODES OF CARRYING OUT THE INVENTION

Figure 1:
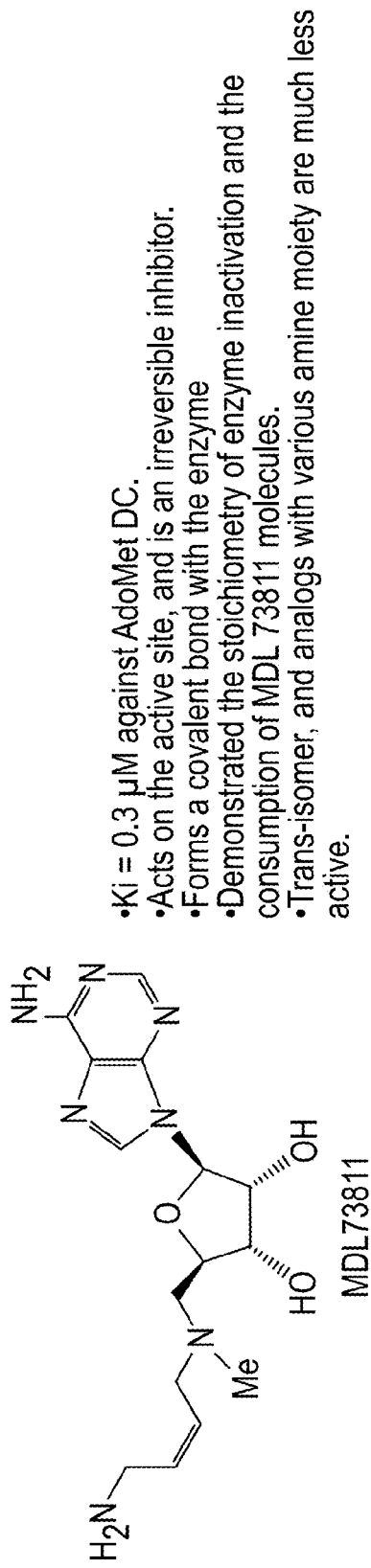
FIG. 1 shows activity information for a representative compound that inhibits SAMDC.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1-2 O, S or N heteroatoms or combinations thereof within the backbone of the residue.

A single alkenyl or alkynyl group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

As used herein, "acyl" encompasses the definitions of alkyl, alkenyl, alkynyl and the related hetero-forms which are coupled to an additional residue through a carbonyl group. Typical examples include formyl, acetyl, acryloyl, and pivaloyl.

As used herein, 'amino' refers to —NH$_2$, and substituted amino encompasses an amino group substituted with one or two alkyl or acyl moieties, or with one amino or alkoxy group and 0-1 alkyl or acyl moieties.

Alkoxy, as used herein, has its ordinary meaning, and refers to an alkyl or substituted alkyl group, typically of 1-6 carbons, that is linked to the molecule through an oxygen atom. Examples include methoxy, isopropoxy, ethoxy, trifluoroethoxy, difluoromethoxy and trifluromethoxy.

The term "cycloalkyl" is used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups As used herein, these terms also include rings that contain a double bond or two, as long as the ring is not aromatic.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

The invention includes compounds of formula (1) as described above. While the compounds are depicted as a single isomer for convenience, the invention includes mixtures of isomers as well as the depicted isomer, e.g., it includes racemic versions of the compound of formula (1), which also possess activity as inhibitors of SAMDC. Formula (1) depicts the relative stereochemistry of substituent groups appended to the ribose ring shown in formula (1); however, where chiral centers are present elsewhere in the molecule, the invention includes each isomer as well as mixtures of isomers at those centers. EP 0472181 A2. P. Casara, et al, *J. Am. Chem. Soc*, (1989), 111, 9111. A. J. Bitoni, et al, *Biochem. J.* (1991), 174, 527. Bacchi, et al, *Antimicrob. Ag. Chemother.* (1992), 36, 2736.

Figure 2:
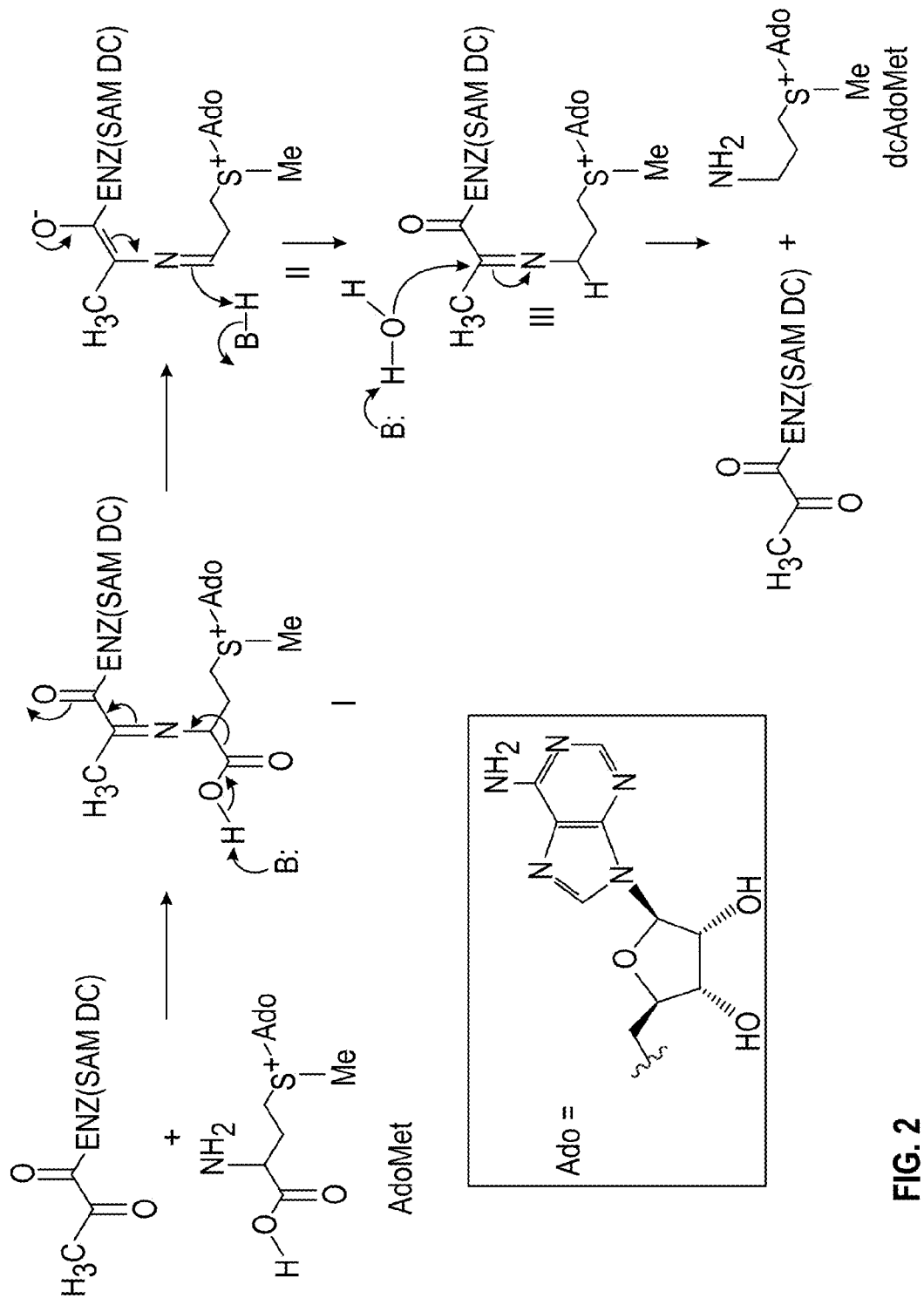
FIG. 2 shows the mechanism by which SAMDC decarboxylates its substrate.

SAM DC is the enzyme which specifically catalyzes the decarboxylation of AdoMet. The proposed mechanism of the reaction is illustrated in FIG. 2. The pyruvoyl moiety of the SAM DC enzyme reacts with the primary amine of AdoMet to form a Schiff base (I). This Shiff base serves as an electron sink to facilitate the decarboxylation, which transforms the substrate into a new, nucleophilic Shiff base (II), which undergoes electron transfer to convert back to a new electrophilic Schiff base (III). From this species, upon hydrolysis, decarboxylated product (dcAdoMet) is released along with free SAM DC.

Figure 3:
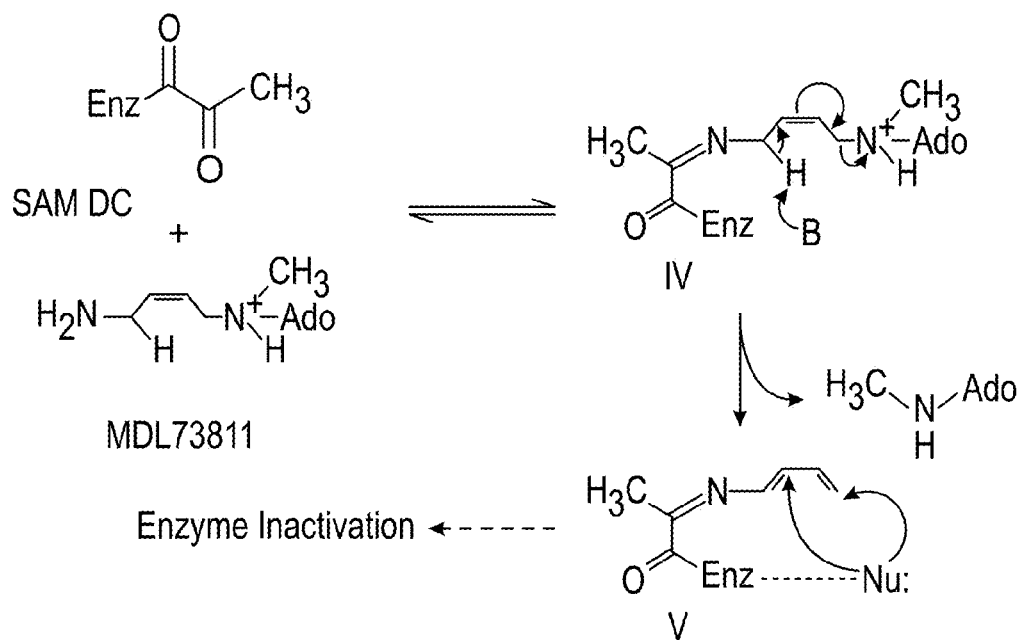
FIG. 3 shows the mechanism by which one compound is believed to inactivate SAMDC.

Work by P. Casara and colleagues identified the mechanism of action of one such compound (see FIG. 3). This compound deactivates SAMDC by targeting the key pyruvoyl group of the enzyme to form a Schiff base (IV), which then undergoes fragmentation initiated by deprotonation at the alpha-position, and consequently forms a highly reactive nucleophilic moiety, N-butadienyl Schiff base (V). This Schiff base can react with any nearby nucleophilic group of the enzyme to form a stable complex (9).

The limitations of the in vivo activity of this compound are attributed to short in vivo half-life ($t_{1/2}$) and poor passage through the blood-brain barrier to reach trypanosomes that infect the CNS. Although causes of short $t_{1/2}$ and poor penetration of brain blood barriers in mice of this compound are unknown, it is hypothesized that the poor PK profile and short duration of the compound in the circulating system might be a primary reason.

In order to improve on the pharmacokinetic properties of MDL73811, the present invention includes modifications of the nucleotide portion of the molecule, to reduce its similarity to adenine in selected ways that cause changes that modulate the PK profile in vivo by reducing its susceptibility to enzymatic transformations by the many enzymes that recognize adenosine as a substrate, while retaining the relatively unique portions of the molecule that support recognition and transformation by SAMDC. The effect such modifications would have was unclear, since SAMDC is a unique enzyme and very little work has been done using 5'-amino-nucleosides as potential drug candidates. Nevertheless, certain compounds of the invention have been shown to exhibit improved biological activity, or better translation of in vitro to in vivo activity.

Based on the proposed mechanism of action, the N-methyl-N-(4-amino)butenylamino moiety of MDL 73811 allows the compound to form a covalent bond with the enzyme and exert suicidal inhibition. The butenylamino group was thus retained, while modifying the other parts of the structure that appear likely to be recognized as substrate by other adenosine-processing enzymes. However, modifications can also be made to the butenyl side chain while retaining or enhancing the ability of the compound to inactivate SAMDC by the same mechanism that MDL73811 uses. Examples of specific butenyl group modifications include these:

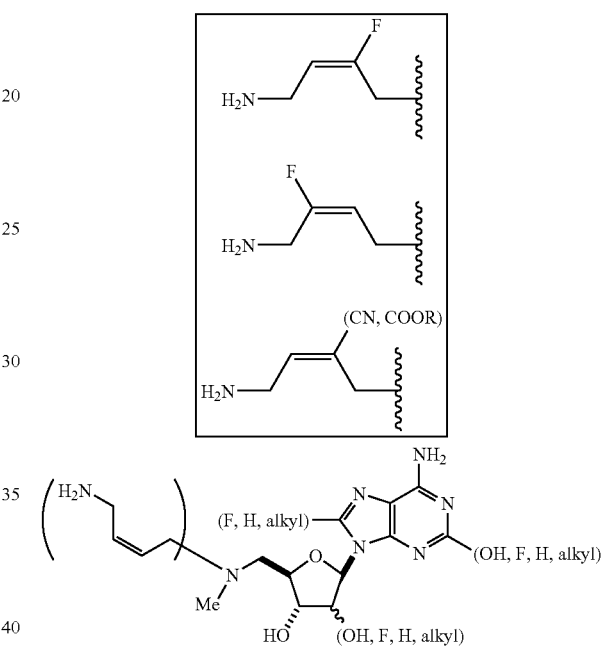

The compounds of the invention can generally be prepared by those of skill in the art using materials and synthetic methods known in the art. Reactions and methods that are useful to prepare the compounds of the invention are disclosed in Hirota, K.; Kitade, Y.; Kanbe, Y.; Maki, Y. *J. Org. Chem.* 1992, 57, 5268; Robins, M. J.; Hansske, F.; Wnuk, S. F.; Kanai, T. *Can. J. Chem.* 1991, 69, 1468; Kawasaki, A. M.; Casper, M. D.; Freier, S. M.; Lesnik, E. A.; Zounes, M. C.; Cummins, L. L.; Gonzalez, C.; Cook, P. D. *J. Med. Chem.* 1993, 36, 831; and Pankiewicz, K. W.; Krzeminski, J.; Ciszewski, L. A.; Ren, W.-Y.; Watanabe, K. A. *J. Org. Chem.,* 1992, 57, 553.

Examples of methods used to synthesize compounds of the present invention are provided below. While the syntheses of specific compounds are used to illustrate approaches to the compounds within the scope of the invention, it is understood by those of skill in the art that modifications of the starting materials and synthesis methods provide access to a wide range of representative inhibitors within the scope of the invention. For example, while specific protecting group strategies are depicted herein, there are many well-known protecting groups that could be used where protection of, e.g., free amine or hydroxyl groups is needed: extensive guidance for selecting, installing and removing such protecting groups is widely available, e.g. in Wuts, et al., *Greene's Protective Groups in Organic Synthesis*, fourth edition (2006).

Scheme 1. Synthesis of 8-methyl-5'-deoxy-N-methyl-N-aminobutenylamino-adenosine.

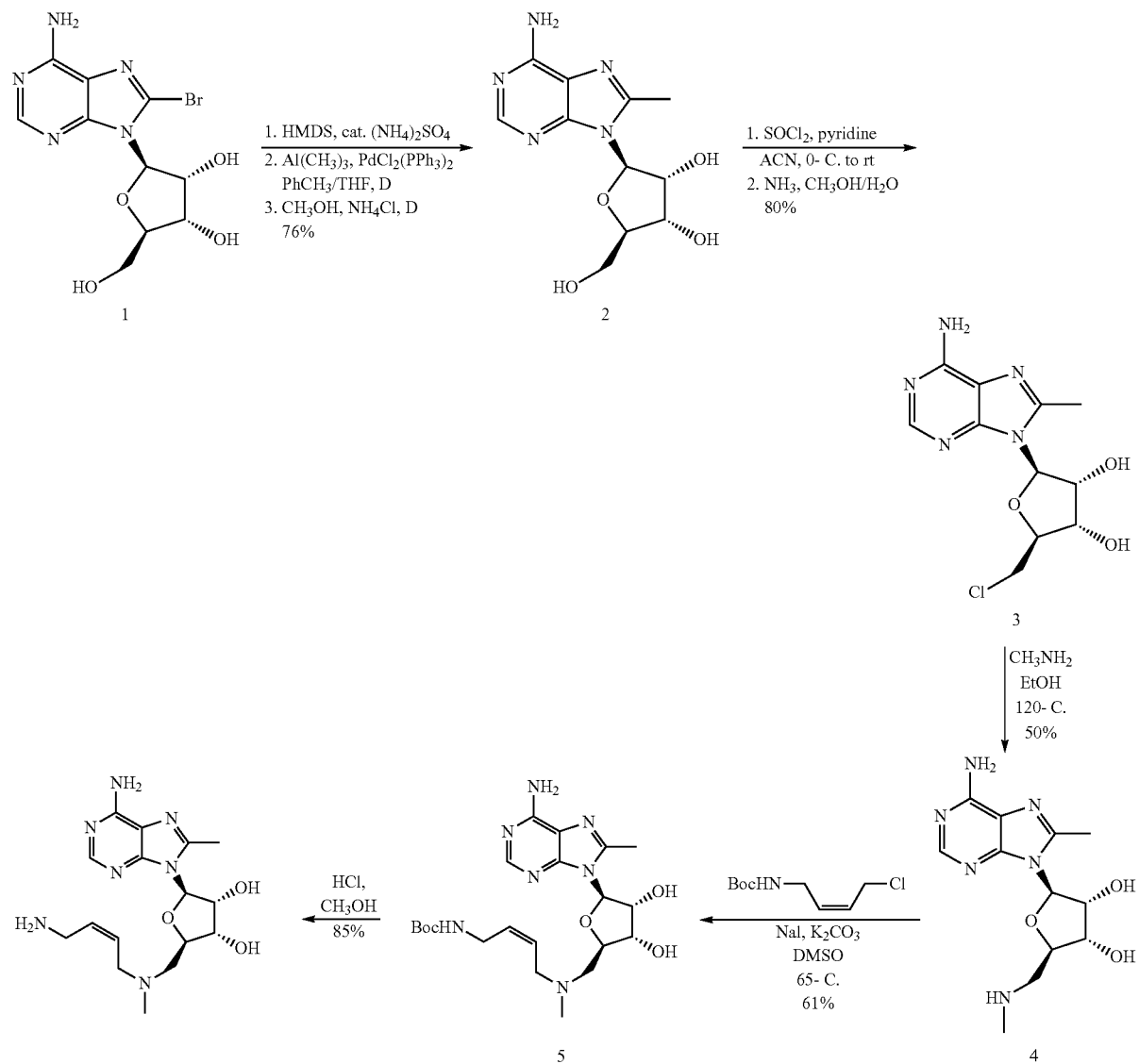

Scheme 1 illustrates a synthesis method useful to prepare many compounds of the invention. It permits various butenyl groups to be incorporated in combination with certain variations of the aromatic moiety of the adenosine portion of the structure.

Scheme 2. Synthesis of 2-chloro-5'-deoxy-N-methyl-N-aminobutenylamino-adenosine.

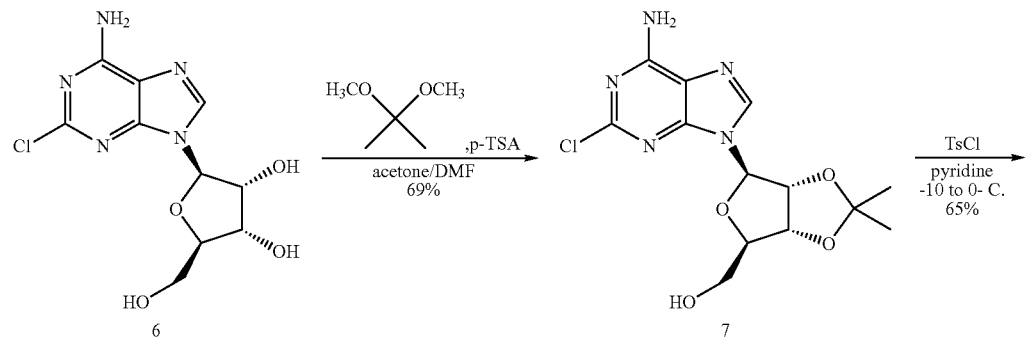

-continued

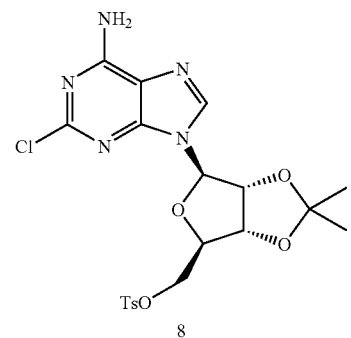

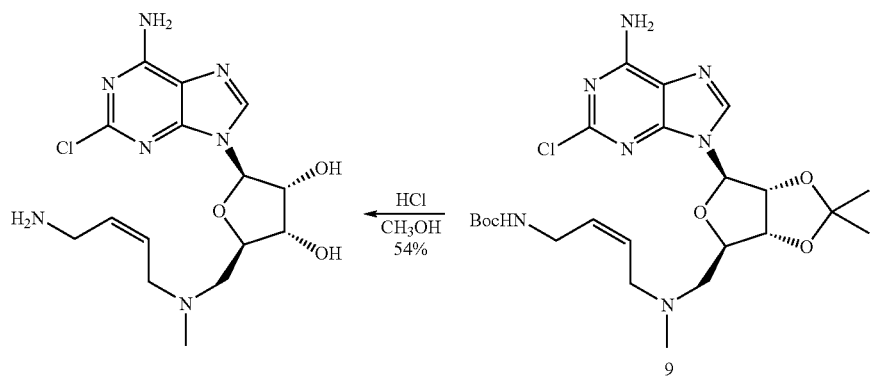

Scheme 2 illustrates another synthesis of compounds of the invention, and shows modification of the aromatic portion of the compound on the pyrimidine ring. It also illustrates one protecting group strategy that permits further modifications to be made after the butenyl group is introduced.

Scheme 3. Synthesis of 2'-deoxy-2' (R)-fluoro-5'-deoxy-N-methyl-N-aminobutenyl-amino-adenosine.

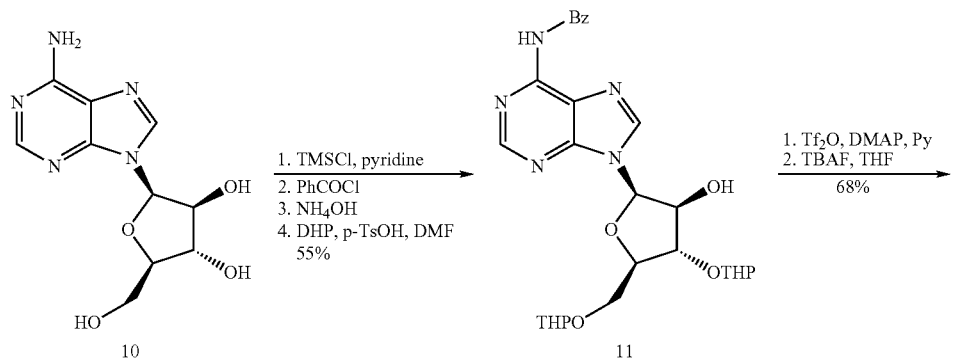

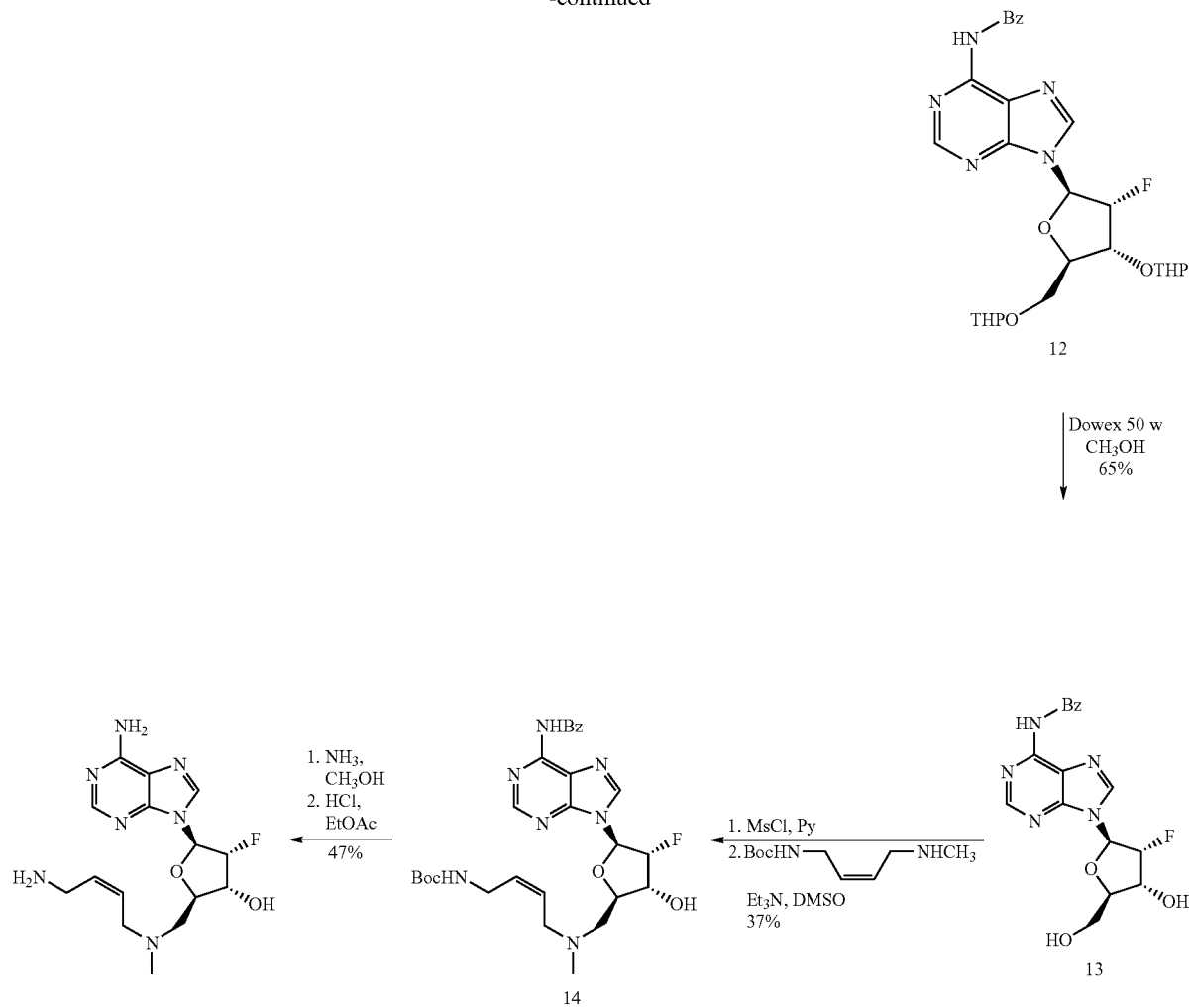
Scheme 3 illustrates another protecting group strategy, which permits selective modification of the hydroxyl groups of the ribose ring portion of the adenosine moiety.
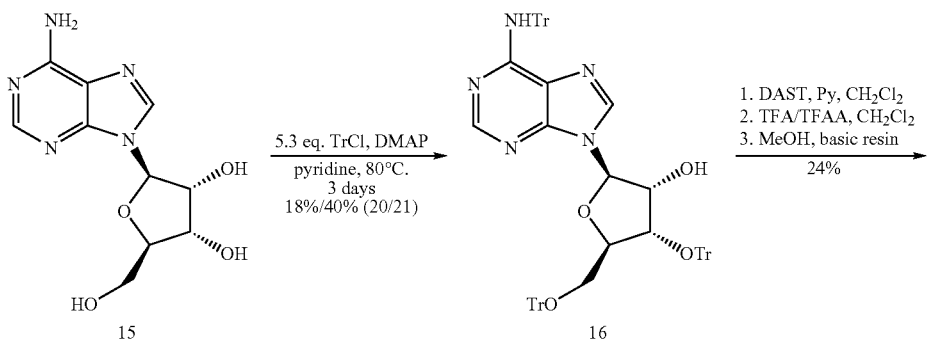

-continued

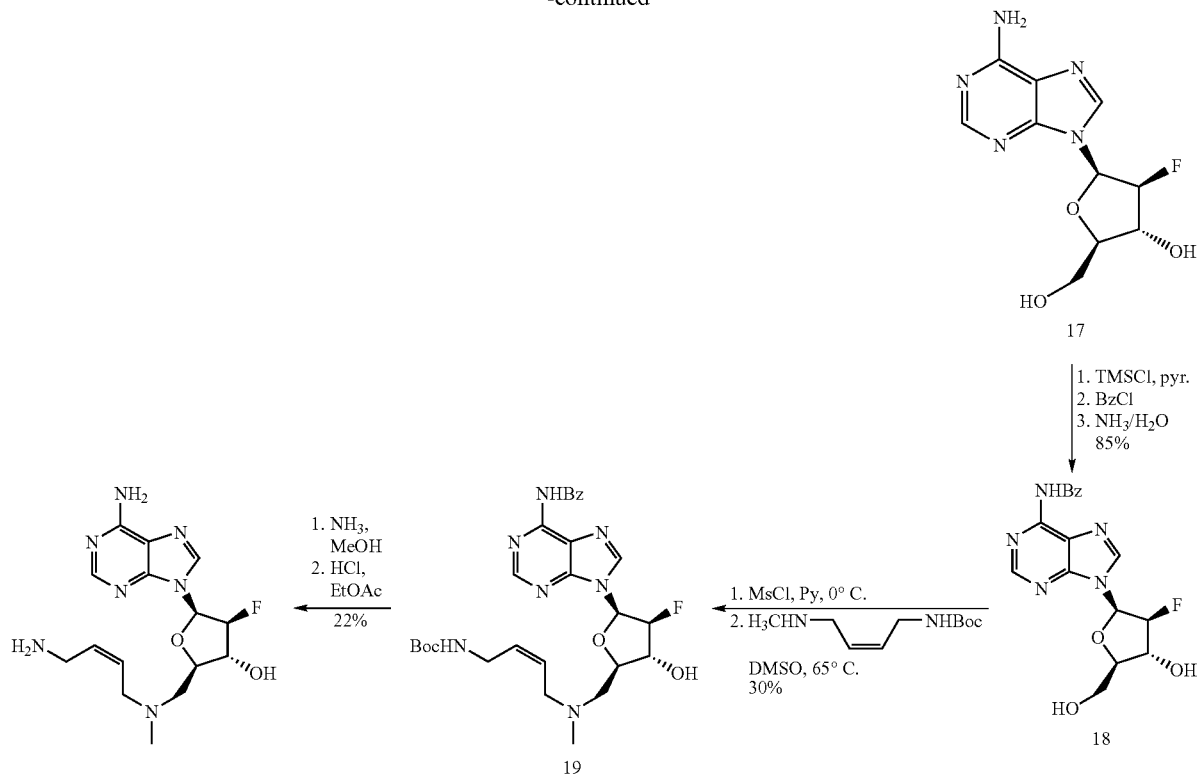

Scheme 4 illustrates another method of modifying the ribose ring portion of these compounds, and demonstrates stereocontrolled synthesis of a compound of the invention, having a fluoro group in place of one of the hydroxyls. This permits modification of part of the molecule that may be subject to metabolism in MDL73811. It also illustrates a method for protecting the amino group of the aromatic portion of the adenosine moiety, to provide a more versatile synthesis method.

In Vitro Biological Assays

*Trypanosoma brucei rhodesiense* strain STIB 900, a clone of a population isolated in 1982 from a patient in Tanzania which is known to be susceptible to all currently used drugs was used in these assays. The bloodstream form trypomastigotes of this strain were maintained in supplemented Modified Eagle's Medium according to standard protocols (Hirumi H, Hirumi K, 1989. "Continuous cultivation of *Trypanosoma brucei* blood stream forms in a medium containing a low concentration of serum protein without feeder cell layers". *J Parasitol* 75: 985-9).

Drug sensitivity assays were performed in sterile 96-well microtiter plates, with or without serial drug dilutions. The compounds were tested at 7 concentrations (drug concentration ranging from 90 μg/ml to 0.123 μg/ml in 3-fold dilutions). The highest concentration for the test compounds was 90 μg/ml. Each drug is tested in duplicate. After 72 hours of incubation the plates were inspected microscopically to assure growth of the controls to determine the minimum inhibitory concentration (MIC), i.e., the lowest drug concentration at which no trypanosomes with normal morphology and motility can be seen compared to control wells. Cell viability is measured by Alamar blue staining and $IC_{50}$ values were calculated.

Enzyme Inhibition Assays

Steady state kinetics were performed as described (Kinch, L. N., J. R. Scott, B. Ullman, and M. A. Phillips. "Cloning and Kinetic Characterization of the *Trypanosoma Cruzi* S-Adenosylmethionine Decarboxylase." *Mol Biochem Parasitol* 101, no. 1-2 (1999): 1-11. Beswick, T. C., E. K. Willert, and M. A. Phillips. "Mechanisms of Allosteric Regulation of *Trypanosoma Cruzi* S-Adenosylmethionine Decarboxylase." *Biochemistry* 45, no. 25 (2006): 7797-807.). This assay measures the amount of $^{14}CO_2$ elaborated by enzymatic cleavage of $^{14}C$-AdoMet. Reactions were carried out in assay buffer (100 mM Hepes pH 8.0, 50 mM NaCl, and 1 mM DTT) using the AdoMetDC/AdoMetDC Prozyme complex at $^{14}C$-AdoMet concentrations of 10-160 μM with saturating putrescine (5 mM) (Willert E K, Phillips M A, 2007. "Allosteric regulation of an essential trypanosome polyamine biosynthetic enzyme by a catalytically dead homolog". *Proc Natl Acad Sci USA* 104: 8275-8280). The reaction components were added to a test tube on ice to a total final volume of 100 μl. The reaction was initiated by the addition of enzyme (1-4 μM for *T. brucei* SAM DC), and a piece of filter paper soaked in saturated barium hydroxide was hung on the side of the test tube, which was then capped with a rubber stopper. Reactions were incubated at 37° C. in a water bath for 5-40 minutes. The assay was stopped by the addition of 200 μl 6 M HCl. The quenched reaction was kept at 37° C. for at least 30 minutes to allow for evolution of the $CO_2$ from the solution. The filter paper was then added to 5 ml of scintillation fluid and counted. Test compounds were assessed over a range of 4 concentrations. Kinetic and regression analysis were performed using GraphPad Prism™.

Three strains of *T. brucei* are used in these studies: (a) *Trypanosoma brucei rhodesiense* STIB 900, a clone of a population isolated in 1982 from a patient in Tanzania which is known to be susceptible to all currently used drugs, (b) *Trypanosoma brucei gambiense* STIB 930, a derivative of strain TH1/78E (031) isolated in 1978 from a patient in Ivory Coast which is known to be sensitive to all drugs used, (c) *Trypanosoma brucei brucei* STIB 950, a clone of a population isolated in 1985 from a bovine in Somalia which shows drug resistance to diminazene, isometamidium and quinapyramine. The bloodstream form trypomastigotes of the three strains are maintained according to standard protocols established at STI.

Drug sensitivity assays are performed in sterile 96-well microtiter plates, with or without serial drug dilutions. The highest concentration for the test compounds is 90 μg/ml. Each drug is tested in duplicate. After 72 hours of incubation the plates are inspected microscopically to assure growth of the controls to determine the minimum inhibitory concentration (MIC), i.e., the lowest drug concentration at which no trypanosomes with normal morphology and motility can be seen compared to control wells. Cell viability is measured by Alamar blue staining and $IC_{50}$ values are calculated.

The preliminary screen used *T. b. rhodesiense*. The compounds were tested at 7 concentrations (drug concentration ranging from 90 μg/ml to 0.123 μg/ml in 3-fold dilutions).

If the $IC_{50}$ is >3 μg/ml, the compound is classified as inactive

If the $IC_{50}$ is 0.2-3 μg/ml, the compound is designated as moderately active If the $IC_{50}$ is <0.2 μg/ml, the compound is classified as active Active compounds ($IC_{50}$<0.2 μg/ml) are tested against the *Trypanosoma brucei gambiense* STIB 930 and the multi-drug resistant *T. b. brucei* STIB 950 following the same protocol as described above.

Compounds are tested for efficacy in the acute model for *T. b. rhodesiense* infection at STI. Briefly, mice are infected with $1 \times 10^4$ trypanosomes on Day 0, then treated once/day (50 mg/kg i.p) with test compound for 4 days starting on Day 3. Animals are assessed by blood smear twice/week through Day 60. Untreated animals generally die by Days 7-9.

Activity Criteria:
Not active: parasitemia remains, survival <15 days
Moderately active: parasitemia disappears temporarily, survival >20 days
Active: parasitemia disappears, survival >60 days In the secondary screen, the minimum curative dose is determined by lowering the daily doses of the 4 day treatment schedule. Size of the groups and activity criteria are the same as above. Dosing will be chosen based upon PK parameters and maximum tolerated doses All four of the 5'-deoxy-N-methyl-N-aminobutenyl-amino-adenosine derivatives prepared above, as well as MDL-73811, have been tested against SAMDC enzyme and in a cell based assay against *Trypanosome b. rhodesiense*. The results are summarized in Table 1.

TABLE 1

Activities of 5'-deoxy-N-methyl-N-aminobutenyl-amino-adenosine derivatives in SAMDC enzyme assay and in cell based antitrypanosomal assay

| ID Supplier | Structure | IC50 against *T. b. rhodesiense* (ug/mL) by STI* | $k_{inact}/Ki^{app}$ against SAM DC enzyme (min$^{-1}$ μM$^{-1}$) by SW** |
|---|---|---|---|
| MDL-73811 | 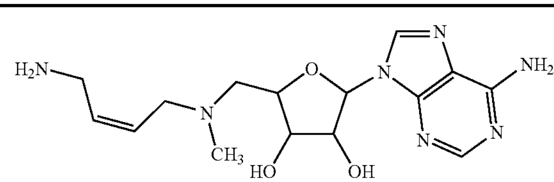 | 0.004 | 1.496 |
| 1 | 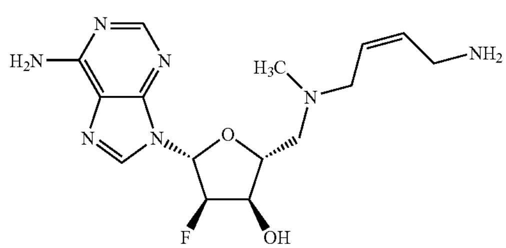 [SMILES: CN(C/C=C\CN)C[C@H]1O[C@@H](n2cnc3c(N)ncnc32)[C@H](F)[C@@H]1O] | 0.489 | 0.192 |
| 2 | 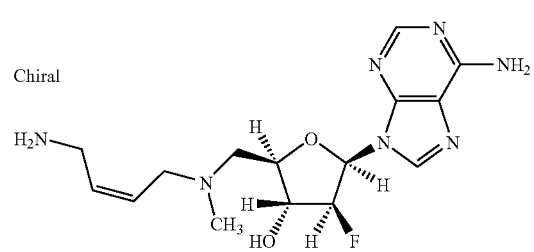 [SMILES: CN(C/C=C\CN)C[C@H]1O[C@@H](n2cnc3c(N)ncnc32)[C@@H](F)[C@@H]1O] | 0.908 | 1.963 |

TABLE 1-continued

Activities of 5'-deoxy-N-methyl-N-aminobutenyl-amino-adenosine derivatives in SAMDC enzyme assay and in cell based antitrypanosomal assay

| ID Supplier | Structure | IC50 against *T. b. rhodesiense* (ug/mL) by STI* | $k_{inact}/Ki^{app}$ against SAM DC enzyme (min$^{-1}$ μM$^{-1}$) by SW** |
|---|---|---|---|
| 3 | 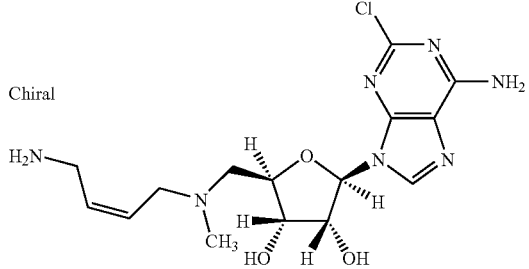 [SMILES: CN(C/C=C\CN)C[C@H]1O[C@@H](n2cnc3c(N)nc(Cl)nc32)[C@H](O)[C@@H]1O] | 0.676 | 0.018 |
| 4 | 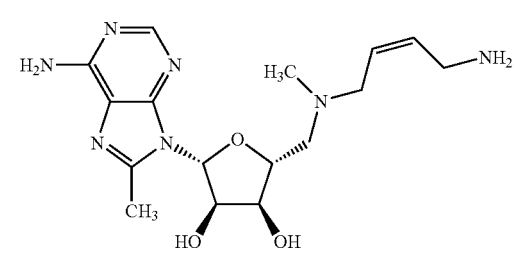 [SMILES: Cc1nc2c(N)ncnc2n1[C@@H]1O[C@H](CN(C)C/C=C\CN)[C@@H](O)[C@H]1O] | 0.0004 | 7.780 |

The compound number 4 in the above table is a more effective SAMDC inhibitor than MDL-73811, based on the values of $k_{inact}/Ki^{app}$. Moreover, this compound shows a higher percentage of brain blood barrier penetration, as discussed below.

The compounds of the invention may be made and used as neutral compounds, or they may be prepared and used as pharmaceutically acceptable salts. In many embodiments, the compounds are made and used as acid addition salts, which are prepared by conventional methods. Selection of pharmaceutically acceptable salts is within the ordinary level of skill in the art; examples of acid addition salts include the hydrochloride, hydrobromide, acetate, succinate, fumarate, mesylate, tosylate, citrate, sulfate, bisulfate, and malate salts as non-limiting examples.

The manner of administration and formulation of the compounds useful in the invention and their related compounds will depend on the nature of the condition, the severity of the condition, the particular subject to be treated, and the judgment of the practitioner; formulation will depend on mode of administration. The particular subject is one having or at risk of having a trypanosomal infection. In most instances, this will be a human being, but livestock as well as companion animals can also be treated.

Compounds of the present invention can conveniently be administered in a pharmaceutical composition containing the compound in combination with a suitable excipient, the composition being useful in combating trypanosomal or protozoal infections. The compounds and compositions of the present invention can be administered parenterally, topically, orally, rectally, intraocularly, or directly into the brain or cerebroventricular space.

As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

For parenteral administration, solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compound can be determined by comparing their in vitro activity or activity in animal models. Activity can be determined by any suitable method. Preferred methods include allometric scaling of effective dosages in animals to humans, and by determining blood levels of drug that are required to achieve the desired effect. These and other methods for the extrapolation of effective dosages to humans are known in the art.

The compound is conveniently administered in unit dosage form; for example, containing 0.1 to 2000 mg, conveniently 100 to 1000 mg, most conveniently, 250 to 750 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

For internal infections, the compositions can be administered orally or parenterally at dose levels, calculated as the free base, of about 0.1 to 100 mg/kg, preferably 1 to 50 mg/kg of mammal body weight, and can be used in man in a unit dosage form, administered one to four times daily.

For parenteral administration, the compounds are presented in aqueous solution in a concentration of from about 0.1 to about 20%, more preferably about 1 to about 5%. The solution may contain other ingredients, such as emulsifiers, antioxidants or buffers.

The exact regimen for administration of the compound and compositions disclosed herein will necessarily be dependent upon the needs of the individual subject being treated, the type of treatment and, of course, the judgment of the attending practitioner.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically in certain situations. Suitable topical formulations include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

It should be noted that the compounds of formula (1) can be administered as individual active ingredients, or as mixtures of several embodiments of this formula. In addition, the inhibitors of SAMDC can be used as single therapeutic agents or in combination with other therapeutic agents. Drugs that could be usefully combined with these compounds include anti-infective with activity against trypanosomes; in particular, combinations with eflornithine (difluoromethyl ornithine), pentamidine, suramin, melarsoprol, or nifurtimox are contemplated. The combination of a compound of the invention with one of these may be administered as separate dosages, or the two materials may be admixed for convenient administration as a single composition.

As implied above, although the compounds of the invention may be used in humans, they are also available for veterinary use in treating animal subjects.

The following examples are intended to illustrate but not to limit the invention.

Example 1

Synthesis of Compound 4

Starting with commercially available 8-bromoadenosine (1), the hydroxyl groups of the ribose moiety were transiently protected by treatment with hexamethyldisilazane and catalytic ammonium sulfate. The crude intermediate underwent palladium catalyzed coupling reaction with trimethylaluminum to install the methyl group at the 8-position. The product, without purification, was deprotected directly to afford 8-methyladenosine derivative (2). Treatment of 2 with thionyl chloride in pyridine afforded the chloride derivative 3, which was subjected to reaction with excess methylamine under microwave irradiation to yields the amine 4. Allylic displacement with cis-1-(t-butoxycarbonylamino)-4-chloro-2-butene under catalytic halide exchange conditions proceeded to form amine 5, which was then deprotected with methanolic hydrogen chloride and purified by silica gel chromatography to afford the final product.

Example 2

Synthesis of Compound No. 3

2-Chloroadenosine (6) was protected as an acetonide (7) by reaction with methyl ketal, and the 5'-hydroxyl was converted a tosylate (8) using tosyl chloride and pyridine. The amine moiety was then introduced through nucleophilic displacement to yield intermediate 9. Deprotection of the BOC group from the primary amine and purification by column chromatography yielded the desired product.

Example 3

Synthesis of Compound No. 1

Araadenosine (10) underwent a series of reactions: silyl protection on the hydroxy groups, benzoylation on the $N^6$, deprotection of silyl groups with ammonium hydroxide, and subsequently protection on the 3'- and 5'-hydroxyls with THP by reaction with DHP in the presence of catalytic amount of pTsOH to provide the protected araadenosine (11). The remaining 2'-hydroxyl was converted to a triflate through the reaction with triflate anhydride, which, without purification, was immediately subjected to TBAF (tetrabutylammonium fluoride) mediated fluoride displacement to afford 12. Acid catalyzed methanolysis removed the THP groups to furnish the N-protected fluoroadenosine intermediate 13, which was selectively mesylated on the 5'-hydroxyl and then displaced by a BOC-protected diamine to generate 14. Deprotection of the benzoyl group at $N^6$ through aminolysis followed by acid catalyzed carbamate cleavage yielded Compound No. 1.

Example 4

Synthesis of Compound No. 2

The preparation of the corresponding arabino fluoro analog proceeded by the method of Kawasaki, et. al. Kawasaki A M, et al., "Uniformly modified 2'-deoxy-2'-fluoro-phosphorothioate oligonucleotides as nuclease-resistant antisense compounds with high affinity and specificity for RNA targets," *J Med Chem* 36: 831-841 (1993). Starting with adenosine (15), reaction with excess trityl chloride afforded a mixture of di- and triprotected compounds. Careful chromatography allowed isolation of the desired, minor tris-trityl compound 16. This material was then subjected to DAST mediated deoxyfluorination, trans-amidation with trifluoroactetic anhydride, and finally, methanolysis to afford the fluoroadenosine 17. At this point, the purine amino group was installed with the same procedures as in the synthesis of Compound No. 1 (Scheme 3) to afford the desired product Compound No. 2.

Example 5

Activity of Inhibitors Again *T. brucei* SAM-DC

Purified, recombinant *T. brucei* SAM-decarboxylase and its prozyme are prepared and assayed in the laboratory of Dr. Phillips according to procedures from that lab. Kinch L N, Scott J R, Ullman B, Phillips M A, "Cloning and kinetic characterization of the *Trypanosoma cruzi* S-adenosylmethionine decarboxylase," *Mol Biochem Parasitol* 101: 1-11. Willert E K, Fitzpatrick R, Phillips M A, 2007 (1999). Briefly, the assay employs $^{14}$C-labelled S-adenosyl methionine ($^{14}$C-

Figure 4:
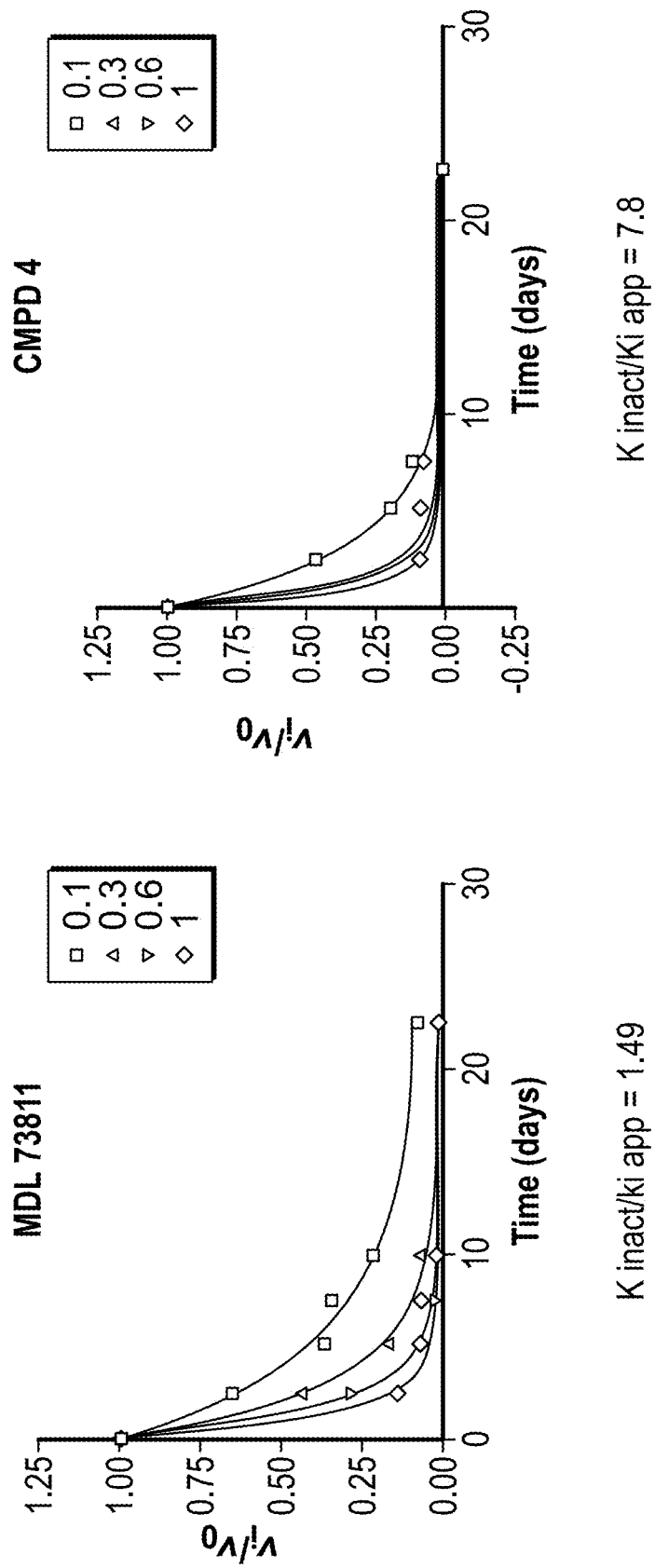
FIG. 4 shows the activity of inhibitors versus *T. brucei* SAMDC enzyme.
Figure 5:
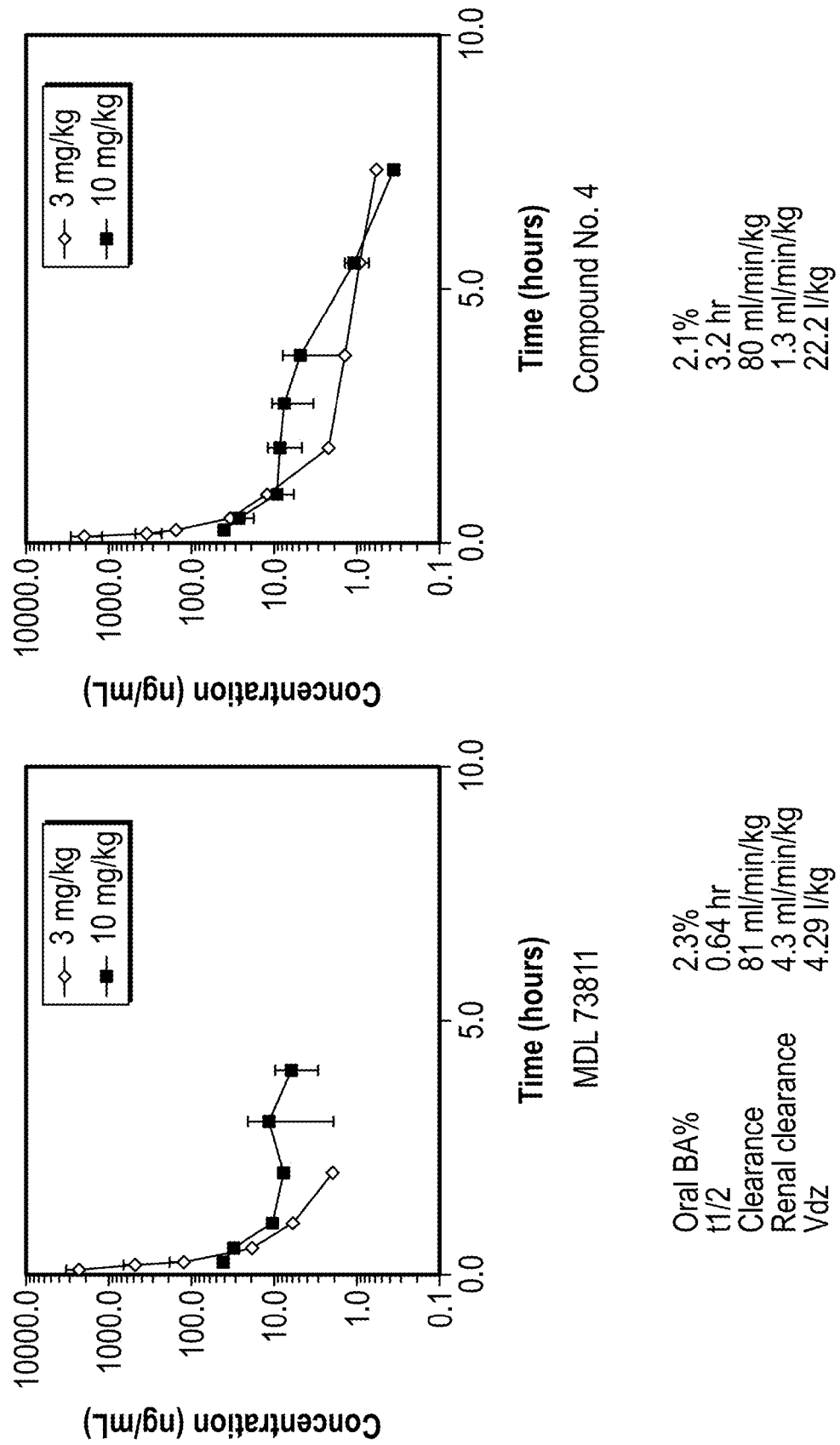
FIG. 5 shows the pharmacokinetics following oral and iv administration in rats.
Figure 6:
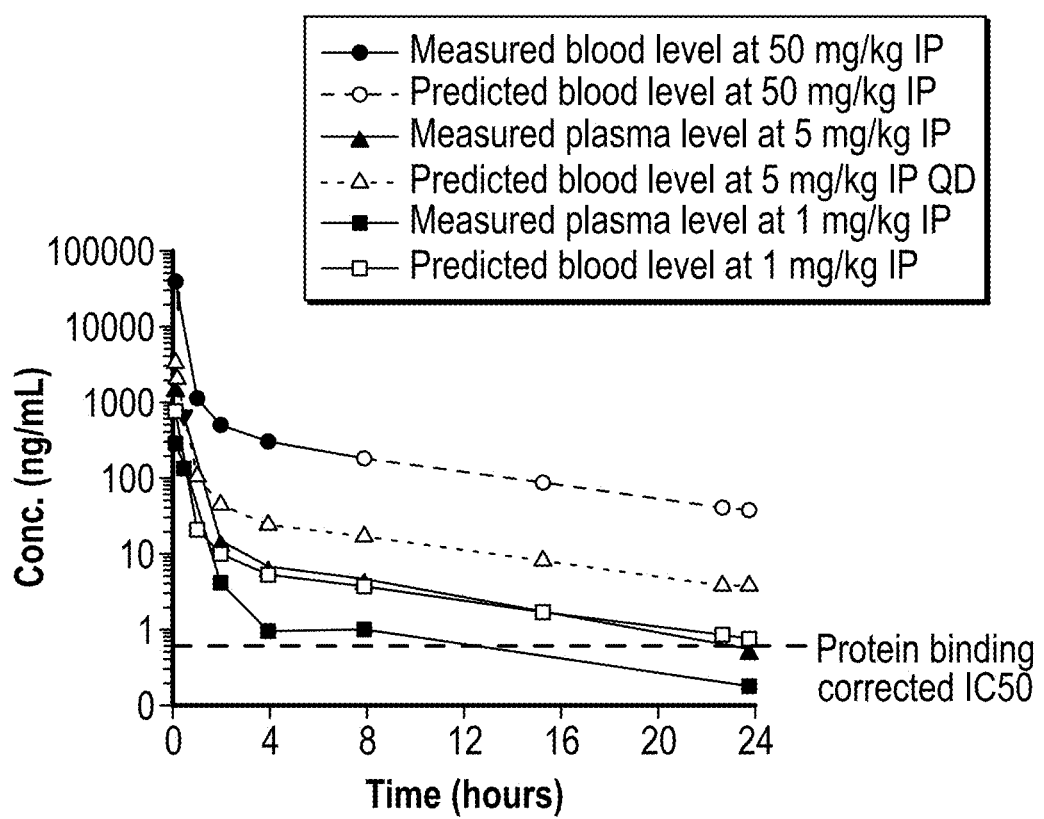
FIG. 6 shows the levels of detectable a compound of the invention at different doses and routes of administration.

AdoMet). Reactions are carried out in buffer (100 mM Hepes pH 8.0, 50 mM NaCl, and 5 mM DTT) at $^{14}$C-AdoMet concentrations of 10-160 µM with saturating putrescine (5 mM). The reaction components are added to a test tube on ice to a total final volume of 100 µl. The reaction is initiated by the addition of enzyme (1-4 µM for *T. brucei* SAM DC), and a piece of filter paper soaked in saturated barium hydroxide is hung on the side of the test tube, which is then capped with a rubber stopper. Reactions are incubated at 37° C. in a water bath for 5-40 minutes. The assay is stopped by the addition of 200 µl 6 M HCl. The quenched reaction is kept at 37° C. for at least 30 minutes to allow for evolution of the $CO_2$ from the solution. The filter paper is then added to 5 ml of scintillation fluid and counted. Test compounds were assessed over a range of 4 concentrations. Kinetic and regression analysis are performed using GraphPad Prism.™ Results of this test are exemplified in FIG. 4.

Example 6

In Vitro ADME Profiles of SAMDC Inhibitors

Solubility

A stock solution for each test compound was prepared at 25 mM in DMSO. These were diluted into phosphate buffer and equilibrated for 16 hours at room temperature, and then filtered to remove precipitated compound. The UV absorbance of this equilibrated sample was compared to a single point reference standard. This test is limited to a solubility range of about 1 to 100 µM, and compounds must have a UV chromophore.

Permeability

A stock solution for each test compound was prepared at 10 mM in DMSO. These were diluted into phosphate buffer and placed on one side (donor) of a two chamber microtiter plate separated by a lipid soaked membrane. With time, the compound passively diffused across the membrane barrier and the concentration in the second chamber (acceptor) increases. At the end of the experiment, drug concentration was determined in both the donor and acceptor solutions by UV absorbance. The permeability was calculated from the change in concentration, surface area, and incubation time. The assay permeability range is ~1 to $50 \times 10^{-6}$ cm/sec, and compounds must have a UV chromophore.

Microsomal/Hepatocyte Stability

Liver microsomes and hepatocytes represent an in vitro surrogate for assessing the phase I/II metabolic stability of new discovery leads. Following the incubation of the compounds with microsomes or hepatocytes of different species (e.g., human, rat, dog, monkey, mouse), the samples were transferred to 96 well plates for quantitation using LC/MS/MS. The % of compound remaining was measured and used to calculate clearance and % hepatic blood flow.

Cytochrome P450 Inhibition

This cytochrome P450 high throughput $IC_{50}$ inhibition assay is utilized for screening potential inhibitors of the 5 major human CYP isozyme catalytic activities (CYP3A4, 2D6, 2C9, 2C19, and 1A2). This method was performed in a 96-well microtiter plate format, which allowed the study of the $IC_{50}$ of 5 test compounds in duplicate and one positive control inhibitor per plate using fluorometric substrates.

Plasma Protein Binding

Rapid Equilibrium Dialysis device (RED) is a 96-well formatted dialysis with disposable inserts and Teflon base design providing short incubation time. The membrane in RED physically separates of bound and free drug. After 4 hr incubation at 37° C., drug concentrations at both plasma (e.g., human, rat, dog, monkey, mouse) and pH 7.4 PBS buffer sides was quantitated by LC/MS/MS and % bound drug in plasma was calculated.

Results (Table 2) show that for all compounds tested, solubility was high, while permeability through artificial membranes was low. All compounds were highly stable in microsome and hepatocyte assays, and protein binding for Compound No. 4 was approximately half that of MDL73811. Compound No. 4 is the most potent of compounds tested, with an $IC_{50}$ against *T. b. rhodesiense* of 0.0004 ug/ml.

Compounds will be assessed for cytotoxicity in mammalian cells. Cell cytotoxicity studies will be done with NHDF (Neonatal human dermal fibroblast cells) in the Alamar Blue assay (AccuMed International Inc), which uses a redox indicator to measure cellular respiration. Test compounds are added to confluent cells and are incubated 18 hr. Alamar Blue is then added, cells are incubated an additional 4 hr, and fluorescence is read at 590 nm.

TABLE 2

In vitro ADME profile of MDL 73811 and selected new compounds.

| ID Supplier | Structure | IC50 against *T. b. rhodesiense* (ug/mL) by STI* | Sol. (ug/ml) | Perm. (10-6 cm/s) | Microsomal stability (CL, mL/min/kg) | | Hepatocyte stability (CL, mL/min/kg) | | CYP IC50 (uM) | Plasma protein binding (%) | |
|---|---|---|---|---|---|---|---|---|---|---|---|
| | | | | | rat | human | rat | human | | human | mouse |
| Genz-642346-1 | H₂N-...-N(CH₃)-...-O-...-(HO)(OH)-...-N=...-NH₂ | 0.004 | >47 (@ 7.4) | 0.13 | <11 | <4.2 | <11 | <4.2 | >5 for 3A4, 2D6, 2C9, 2C19, 1A2 | 72.9 | 69.8 |

TABLE 2-continued

In vitro ADME profile of MDL 73811 and selected new compounds.

| ID Supplier | Structure | IC50 against *T. b. rhodesiense* (ug/mL) by STI* | Sol. (ug/ml) | Perm. (10-6 cm/s) | Microsomal stability (CL, mL/min/kg) | | Hepatocyte stability (CL, mL/min/kg) | | CYP IC50 (uM) | Plasma protein binding (%) | |
| --- | --- | --- | --- | --- | --- | --- | --- | --- | --- | --- | --- |
| | | | | | rat | human | rat | human | | human | mouse |
| Genz-643990-1 | 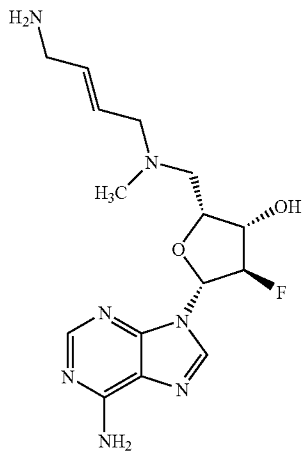 [SMILES: CN(C/C=C/CN)C[C@H]1O[C@@H](n2cnc3c(N)ncnc32)[C@H](F)[C@H]1O] | 0.489 | >47 (@ 7.4) | 0.00 | <11 | <4.2 | <11 | <4.2 | >5 for 3A4, 2D6, 2C9, 2C19, 1A2 | 23.3 | 47.7 |
| Genz-644043-1 | Chiral | 0.908 | >47 (@ 7.4) | 0.00 | <11 | <4.2 | <11 | <4.2 | >5 for 3A4, 2D6, 2C9, 2C19, 1A2 | 32.2 | 37.2 |
| Genz-644053-1 | Chiral | 0.676 | >51 (@ 7.4) | 0.36 | <11 | <4.2 | <11 | <4.2 | >5 for 3A4, 2D6, 2C9, 2C19, 1A2 | 39.0 | 42.2 |

TABLE 2-continued

In vitro ADME profile of MDL 73811 and selected new compounds.

| ID Supplier | Structure | IC50 against T. b. rhodesiense (ug/mL) by STI* | Sol. (ug/ml) | Perm. (10-6 cm/s) | Microsomal stability (CL, mL/min/kg) | | Hepatocyte stability (CL, mL/min/kg) | | CYP IC50 (uM) | Plasma protein binding (%) | |
|---|---|---|---|---|---|---|---|---|---|---|---|
| | | | | | rat | human | rat | human | | human | mouse |
| Genz-644131-1 | 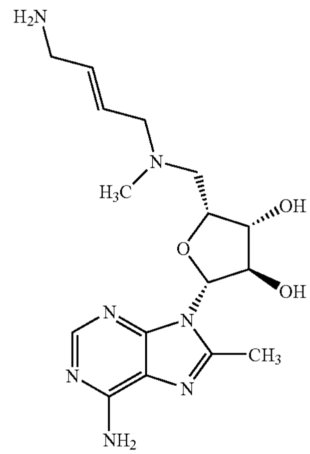 [SMILES: Cc1nc2c(N)ncnc2n1[C@@H]1O[C@H](CN(C)C/C=C/CN)[C@H](O)[C@H]1O] | 0.00040 | >49 (@ 7.4) | 0.22 | <11 | <4.2 | <11 | <4.2 | >5 for 3A4, 2D6, 2C9, 2C19, 1A2 | 41.2 | 35.7 |

Example 7

In Vivo Properties and Activity of SAMDC Inhibitors

The routine mouse PK study design uses 6 serial tail bleeds and one terminal bleed within 24 hr following the administration of a test compound. The rodent PK study designs provide reliable estimation of PK parameters using fewer animals. Often two routes, PO and IV, were included in the rodent PK study protocols with three subjects in each dosing group (often PO at 10 mg/kg and IV at 3 mg/kg).

Mouse Brain Exposure:

This was determined by harvesting brains at selected time points, weighing and extracting total tissue homogenate for LC/MS/MS analysis. The amount of test compound associated with the brain was calculated by subtracting that amount attributable to blood vessels (7%, times the blood exposure levels).

Results (Table 3) show that mouse brain exposure for Compound No. 4 is ~4-fold greater than for MDL 73811 and t/2 for it was ~3-fold greater than that for MDL-73811. Finally, potency of this compound was 10-fold greater against T. b. brucei than that of MDL73811.

TABLE 3

| Compound | Mouse Brain Exposure AUC (mg*hr/mL) | Mouse Brain exposure compared with blood AUC (%) | t/2 in mouse (hr) | IC50 against T. brucei rhodesiense (mg/mL) |
|---|---|---|---|---|
| MDL 73811 | 0.28 | 1.34 | 2.48 | 0.004 |
| Compound 1 | 0.026 | 0.16 | 1.93 | 0.489 |
| Compound 3 | 0.17 | 0.77 | 1.66 | 0.967 |
| Compound 4 | 1.18 | 6.60 | 7.43 | 0.0004 |

Example 8

In Vivo Efficacy

Compounds are tested for efficacy in the acute model for T. b. brucei infection (Bitonti A J, Byers T L, Bush T L, Casara P J, Bacchi C J, Clarkson A B, Jr., McCann P P, Sjoerdsma A, 1990. Cure of Trypanosoma brucei brucei and Trypanosoma brucei rhodesiense infections in mice with an irreversible inhibitor of S-adenosylmethionine decarboxylase. Antimicrob Agents Chemother 34: 1485-1490). Briefly, mice are infected with $1 \times 10^4$ strain STIB 795 trypanosomes on Day 0, then treated once/day (50 mg/kg i.p) with test compound for 4 days starting on Day 3. Animals are assessed by microscopic examination of blood smears twice/week through Day 60. Untreated animals generally die by Days 7-9.

To determine compound efficacy in the CNS model of disease, the GVR 35 strain of T. b. brucei is used according to the methods of Jennings and Gray (Jennings F W, Gray G D, 1983. Relapsed parasitaemia following chemotherapy of chronic T. brucei infections in mice and its relation to cerebral trypanosomes. Contrib Microbiol Immunol 7: 147-154). Briefly, mice are injected i.p. with $2 \times 10^4$ trypanosomes on Day 0. Test compounds are administered daily from Day 21 through Day 25, and parasitemia is evaluated 2x/week by microscopic examination of blood smears from Day 28-Day 50. Weekly assessments are continued through Day 180 post-infection. Cure is deemed effective in the absence of recurring parasitemia.

Results (Table 4) show that both MDL 73811 and Compound No. 4 protected mice from lethal effects of infection. Control animals (non-treated) died on average by Day 6 post-infection, while treated animals all survived through Day 30. Further, on Day 20, animals treated with Compound No. 4 appeared free of parasites, although parasites were again evident on Day 30.

TABLE 4

Efficacy Data of MDL 73811 & Compound No. 4 in STIB795 model.
T. b. brucei - STIB795    conc.: 1 × 10 4/mouse (NMRI)

| compound | dose mg/kg | injection | cured/ infected | cured/ infected | average |
|---|---|---|---|---|---|
| Control | — | — | 0/4 | 0/4 | 6 |
| MDL 73811 | 4 × 50 | i.p. | 26 Days 2/4 | >30 Days 1/4 | >30 days |
| CMPD 4 | 4 × 50 | i.p. | 20 Days 0/4 | >30 Days 1/4 | >30 days |

Both MDL73811 and Compound No. 4 were active in the model in terms of lengthening the survival days; but only cured 1/4 mice.

Example 9

Compound 5: Characterization and Synthesis

This example provides characterization data and synthetic guidance for synthesized compound number 5 shown here:

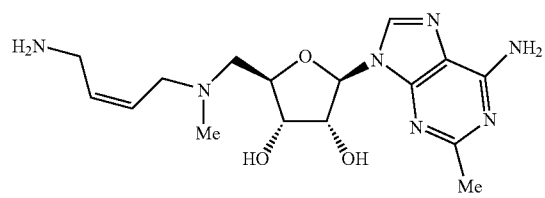 [SMILES: Cc1nc(N)c2ncn([C@@H]3O[C@H](CN(C)C/C=C\CN)[C@@H](O)[C@H]3O)c2n1]

Characterization data: $^1$H NMR (CD$_3$OD, 400 MHz) δ 8.25 (s, 1H), 6.04 (d, J=4.4 Hz, 1H), 5.98-5.90 (m, 2H), 4.79 (t, J=4.4 Hz, 2H), 4.47-4.43 (m, 2H), 3.87 (d, J=5.2 Hz, 2H), 3.71-3.68 (m, 2H), 3.63 (dd, J=9.2, 13.6 Hz, 1H), 3.49 (d, J=13.6 Hz, 1H), 2.81 (s, 3H), 2.51 (s, 3H); MS m/z 364.3 (M+H)$^+$.

In preparation of compound 5, the intermediate compound, 2-methyl adenosine, can be synthesized by the following procedure.

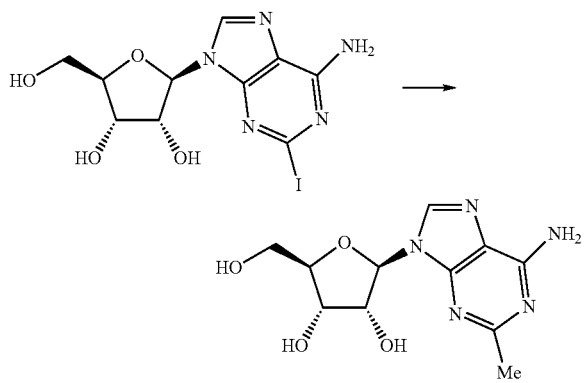

A solution of 2-iodoadenosine (1 g, 2.5 mmol) and ammonium sulfate (0.033 g, 0.25 mmol) in hexamethyldisilazane (20 mL) was heated overnight at 80° C. The reaction was cooled to room temperature, concentrated in vacuo, and azeotroped with toluene. The residue was taken up in THF (10 mL) and Pd(PPh$_3$)$_4$ (0.144 g, 0.125 mmol) was added. The reaction mixture was heated at 68° C. for 10 minutes before the addition of trimethylaluminum (2.0M in hexanes, 5.0 mL, 5.0 mmol). Heating was continued for 3.5 h. After cooling to room temperature, MeOH was added to destroy excess trimethylaluminum. The reaction mixture was partitioned between CHCl$_3$ and H$_2$O. The aqueous layer was extracted with CHCl$_3$ (2×50 mL). The combined organic layers were washed with brine, dried over MgSO$_4$, and concentrated in vacuo. The residue was taken up in MeOH:H$_2$O (4:1) (25 mL) and ammonium chloride was added (400 mg). The reaction was heated at 65° C. for 3 h. When judged complete by TLC, the reaction was concentrated in vacuo and was subjected to silica gel column chromatography running 2% MeOH:DCM with 0.1% NH$_4$OH to afford 2-methyl adenosine.

The 2-methyl adenosine intermediate can be used to prepare Compound 5 by following the general route detailed in Scheme 1.

Example 10

Compound 6: Characterization and Synthesis

This example provides characterization data and synthetic guidance for the synthesized compound number 6 shown here:

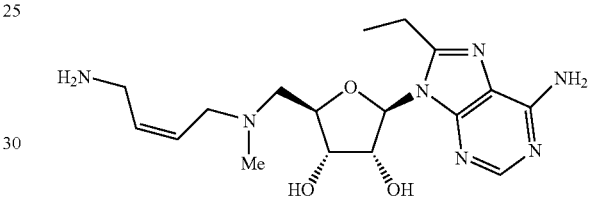

Characterization data: $^1$H NMR (CD$_3$OD, 400 MHz) δ 8.21 (s, 1H), 6.01 (d, J=6.0 Hz, 1H), 5.99-5.89 (m, 2H), 5.11 (t, J=5.6 Hz, 1H), 4.53-4.49 (m, 1H), 4.46-4.44 (m, 1H), 4.01 (d, J=6.8 Hz, 2H), 3.86 (dd, J=10.8, 12.8 Hz, 1H), 3.73 (t, J=6.8 Hz, 2H), 3.57 (dd, J=2.4, 12.8 Hz, 1H), 3.00 (q, J=7.2 Hz, 2H), 2.90 (s, 3H), 1.43 (t, J=7.2 Hz, 3H); MS m/z 378.4 (M+H)$^+$.

In preparation of compound 6, the intermediate compound, 8-ethyl adenosine, can be synthesized by the following procedure.

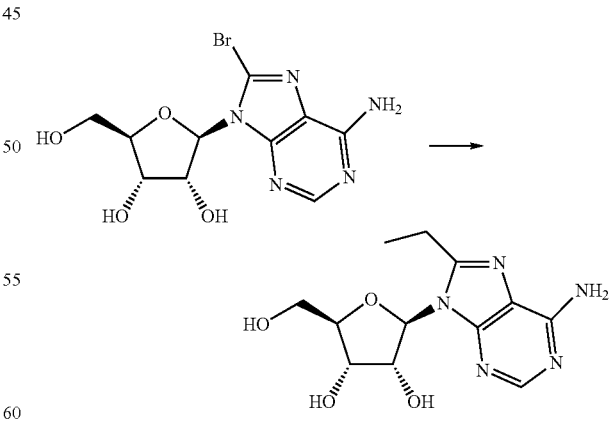

A solution of 8-Bromoadenosine (0.5 g, 1.5 mmol) and hexamethyldisilazane (5 mL) in 1,4-dioxane (10 mL) was heated overnight at 80° C. The reaction was cooled to room temperature, concentrated in vacuo, and azeotroped with toluene. The residue was taken up in NMP (3 mL) and tetraethyltin (0.59 mL, 3.0 mmol) and Pd(PPh$_3$)$_4$ (0.175 g, 0.15 mmol) were added. The reaction was allowed to stir at 130° C. for 16 h before cooling to room temperature. The reaction mixture was partitioned between H₂O and EtOAc. The aqueous layer was extracted with EtOAc (2×20 mL). The combined organic layers were washed with brine, dried over MgSO₄, and concentrated in vacuo. The residue was taken up in MeOH:H₂O (4:1) (25 mL) and ammonium chloride was added (400 mg). The reaction was heated at 65° C. for 3 h. When judged complete by TLC, the reaction was concentrated in vacuo and was subjected to silica gel column chromatography running 0-25% MeOH:DCM with 0.1% NH₄OH to afford 8-ethyl adenosine.

The 8-ethyl adenosine intermediate can be used to prepare Compound 6 by following the general route detailed in Scheme 1.

Example 11

Compound 7: Characterization and Synthesis

This example provides characterization data and synthetic guidance for the synthesized compound number 7 shown here:

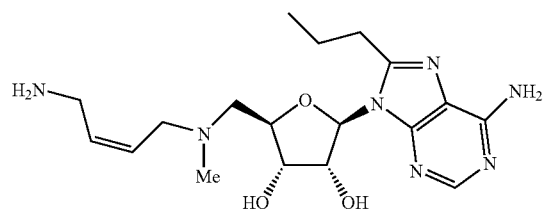 [SMILES: CCCc1nc2c(N)ncnc2n1[C@@H]1O[C@H](CN(C)C/C=C\CN)[C@@H](O)[C@H]1O]

Characterization data: ¹H NMR (CD₃OD, 400 MHz) δ 8.14 (s, 1H), 5.95-5.88 (m, 1H), 5.90 (d, J=4.8 Hz, 1H), 5.76-5.72 (m, 1H), 5.15 (t, J=5.2 Hz, 1H), 4.41 (t, J=5.2 Hz, 1H), 4.27-4.23 (m, 1H), 3.53 (d, J=6.8 Hz, 2H), 3.36-3.29 (m, 1H), 3.16 (dd, J=9.2, 12.8 Hz, 1H), 2.94 (t, J=7.6 Hz), 2.92-2.88 (m, 1H), 2.40 (s, 3H), 1.92-1.86 (m, 2H), 1.07 (t, J=7.6 Hz, 3H); MS m/z 392.4 (M+H)⁺.

In preparation of compound 7, the intermediate compound, 8-ethyl adenosine, can be synthesized by the following procedure.

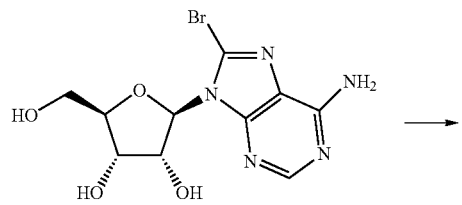

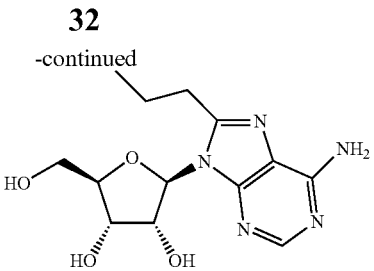

A solution of 8-Bromoadenosine (0.5 g, 1.5 mmol) and hexamethyldisilazane (5 mL) in 1,4-dioxane (10 mL) was heated overnight at 80° C. The reaction was cooled to room temperature, concentrated in vacuo, and azeotroped with toluene. The residue was taken up in NMP (3 mL) and tri-n-butylpropenyltin (1.0 g, 3.0 mmol) and Pd(PPh₃)₄ (0.175 g, 0.15 mmol) were added. The reaction was heated at 190° C. under microwave conditions for 0.5 h before cooling to room temperature. The catalyst was filtered through celite washing with EtOAc. The filtrate was partitioned between H₂O and EtOAc. The aqueous layer was extracted with EtOAc (2×20 mL). The combined organic layers were washed with brine, dried over MgSO₄, and concentrated in vacuo. The residue was taken up in MeOH:H₂O (4:1) (25 mL) and ammonium chloride was added (400 mg). The reaction was heated at 65° C. for 3 h. When judged complete by TLC, the reaction was concentrated in vacuo and was subjected to silica gel column chromatography running 0-25% MeOH:DCM with 0.1% NH₄OH to afford 8-propenyl adenosine. The compound from the previous step was taken up in EtOH:H₂O (3:1) (4 mL) and TFA (5 drops) and hydrogenated under H₂ atmosphere in the presence of Pd/C 10% (20% w/w) at room temperature overnight. The catalyst was filtered off and the filtrate evaporated in vacuo. The 8-propyl adenosine was used without further purification.

The 8-propyl adenosine intermediate can be used to prepare Compound 7 by following the general route detailed in Scheme 1.

Example 12

Biological Assays and In Vitro ADME Profiling of Compounds

This example provides data relating to the biological screening results. MDL 73811 and selected new compounds 1-7 were tested against a variety of cell-based organisms and enzymes and the IC₅₀ measured. In vitro ADME profiles were also obtained. Solubility, permeability, microsomal/hepatocyte stability, cychrome P450 inhibition and plasma protein binding characteristics were probed for each of the compounds. The methodology for these tests are described in previous paragraphs. The results are summarized in the following 2 charts.

| | | Screening Data (IC50) uM | | | | IC50 Schistosomes | |
|---|---|---|---|---|---|---|---|
| Compound | Substitution | T. b. brucei | T. b. rhod. | T. cruzi | L. donovani (axenic) | adult | lavae |
| | MDL-73811 | 0.171 0.257 | 0.011 | 19.39 | >85 | >10 | >10 |
| 1 | 1'(R)-F | >14 >14 | 1.39 | >85 | >85 | >10 | >10 |

-continued

| | | Screening Data (IC50) uM | | | | | |
|---|---|---|---|---|---|---|---|
| | | | | | *L. donovani* | IC50 Schistosomes | |
| Compound | Substitution | *T. b. brucei* | *T. b. rhod.* | *T. cruzi* | (axenic) | adult | lavae |
| 2 | 1'(S)-F | >14<br>>14 | 2.59 | >85 | >85 | >10 | >10 |
| 3 | 2-Cl | 8.57<br>5.96 | 1.76 | >85 | >85 | >10 | >10 |
| 4 | 8-Me | 0.027<br>0.027 | 0.001 | >85 | >85 | >10 | >10 |
| 5 | 2-Me | >14<br>>14 | | | | >10 | >10 |
| 6 | 8-Et | 1.16<br>0.64 | | | | >10 | >10 |
| 7 | 8-Pr | 12.69<br>9.40 | | | | >10 | >10 |

| | | | | | Microsomes | | Hepatocytes | | | | | | | | |
|---|---|---|---|---|---|---|---|---|---|---|---|---|---|---|---|
| Compound | Substitution | Solubility @pH = 7.4 (ug/mL) | Permeability (10−6 cm/sec) | LogD | Rat Clint (mL/min/kg) | Human Clint (mL/min/kg) | Rat Clint (mL/min/kg) | Human Clint (mL/min/kg) | CYP IC50 uM | | | | | Plasma Protein Binding % | |
| | | | | | | | | | 1A2 | 2C19 | 2C9 | 2D6 | 3A4 | human | mouse |
| | MDL-73811 | >47 | 1.1 | −1.8 | <7.7 | <4.5 | <3.5 | <1.7 | >5 | >5 | >5 | >5 | >5 | 72.9 | 69.8 |
| 4 | 8-Me | >49 | 0.22 | −1.4 | <7.7 | <4.5 | <3.5 | <1.7 | >5 | >5 | >5 | >5 | >5 | 41.2 | 35.7 |
| 6 | 8-Et | >51 | 0 | <1.0 | N/A | N/A | N/A | N/A | >5 | >5 | >5 | >5 | >5 | N/A | N/A |
| 3 | 2-Cl | >51 | 0.36 | N/A | <7.7 | <4.5 | <3.5 | <1.7 | >5 | >5 | >5 | >5 | >5 | 39 | 42.2 |
| 7 | 8-Pr | >52 | 0 | <1.0 | N/A | N/A | N/A | N/A | >5 | >5 | >5 | >5 | >5 | N/A | N/A |
| 1 | 1'(R)-F | >47 | 0 | −1.3 | <7.7 | <4.5 | <3.5 | <1.7 | >5 | >5 | >5 | >5 | >5 | 23.3 | 47.7 |
| 2 | 1'(S)-F | >47 | 0 | −1.2 | <7.7 | <4.5 | <3.5 | <1.7 | >5 | >5 | >5 | >5 | >5 | 32.2 | 37.2 |
| 5 | 2-Me | >49 | 0 | <1.0 | N/A | N/A | N/A | N/A | >5 | >5 | >5 | >5 | >5 | N/A | N/A |

The invention claimed is:

1. A compound of formula (1) or a pharmaceutically acceptable salt thereof,

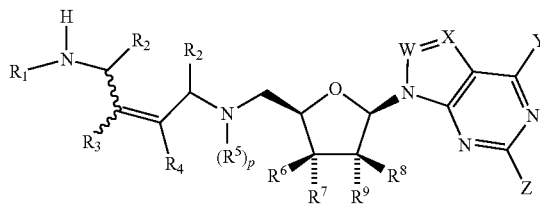

(1)

wherein:
W is N or $CR^{10}$;
X is N or $CR^{10}$;
Y is $NHR^1$;
Z is H, F, Cl, $OR^1$, $CF_3$, or optionally substituted alkyl;
$R^1$ is, independently at each occurrence, H, acyl, alkyl, alkenyl, alkynyl, cycloalkyl, heterocyclyl, aryl, heteroaryl, or alkoxyacyl, wherein each acyl, alkyl, alkenyl, alkynyl, cycloalkyl, heterocyclyl, aryl, heteroaryl, or alkoxyacyl is substituted or unsubstituted;
$R^2$ is, independently at each occurrence, H, substituted or unsubstituted acyl, or substituted or unsubstituted alkyl;
$R^3$ and $R^4$ are each independently H, F, Cl, CN, or COOR, where R is H or C1-C8 alkyl; or $R^3$ and $R^4$ taken together form a bond;
$R^5$ is H, acyl, alkyl, alkenyl, alkynyl, amino, alkoxy, or alkoxyacyl, wherein each acyl, alkyl, alkenyl, alkynyl, amino, alkoxy, or alkoxyacyl is substituted or unsubstituted;
$R^6$ and $R^8$ are each independently H, OH, F, alkoxy, or alkyl, wherein each alkoxy, or alkyl is substituted or unsubstituted;
$R^7$ is OH, F, alkoxy, or alkyl, wherein each alkoxy or alkyl is substituted or unsubstituted;
$R^9$ is OH, F, alkoxy, or alkyl, wherein each alkoxy or alkyl is substituted or unsubstituted; or $R^9$ is H when $R^8$ is F; and
$R^{10}$ is, independently at each occurrence, H, CN, $CF_3$, alkyl, alkenyl, alkynyl, or acyl, wherein each alkyl, alkenyl, alkynyl, or acyl is substituted or unsubstituted;
provided that $R^7$ and $R^9$ are not both OH when W is CH, X is N, and Z is H.

2. The compound of claim 1, wherein W is $CR^{10}$, where $R^{10}$ is not H.
3. The compound of claim 1, wherein W is N.
4. The compound of claim 1, wherein X is N.
5. The compound of claim 1, wherein X is $CR^{10}$.
6. The compound of claim 1, wherein Y is $NH_2$.
7. The compound of claim 1, wherein Z is H, F, or Cl.
8. The compound of claim 1, wherein $R^5$ is C1-C4 alkyl.
9. The compound of claim 1, wherein at least one of $R^6$, $R^7$, $R^8$ and $R^9$ is F.
10. The compound of claim 1, wherein each $R^2$ is H.
11. The compound of claim 1, wherein $R^3$ and $R^4$ are each hydrogen, and $R^3$ and $R^4$ are in a cis relationship.

12. A compound selected from the group consisting of:

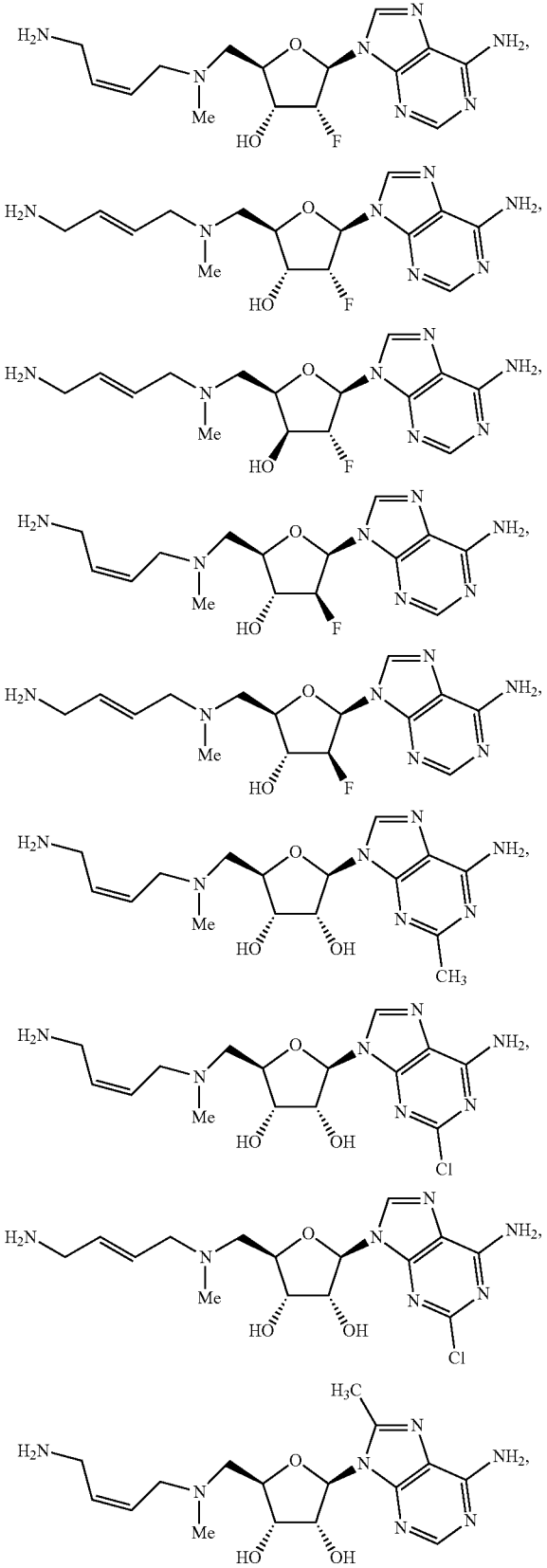
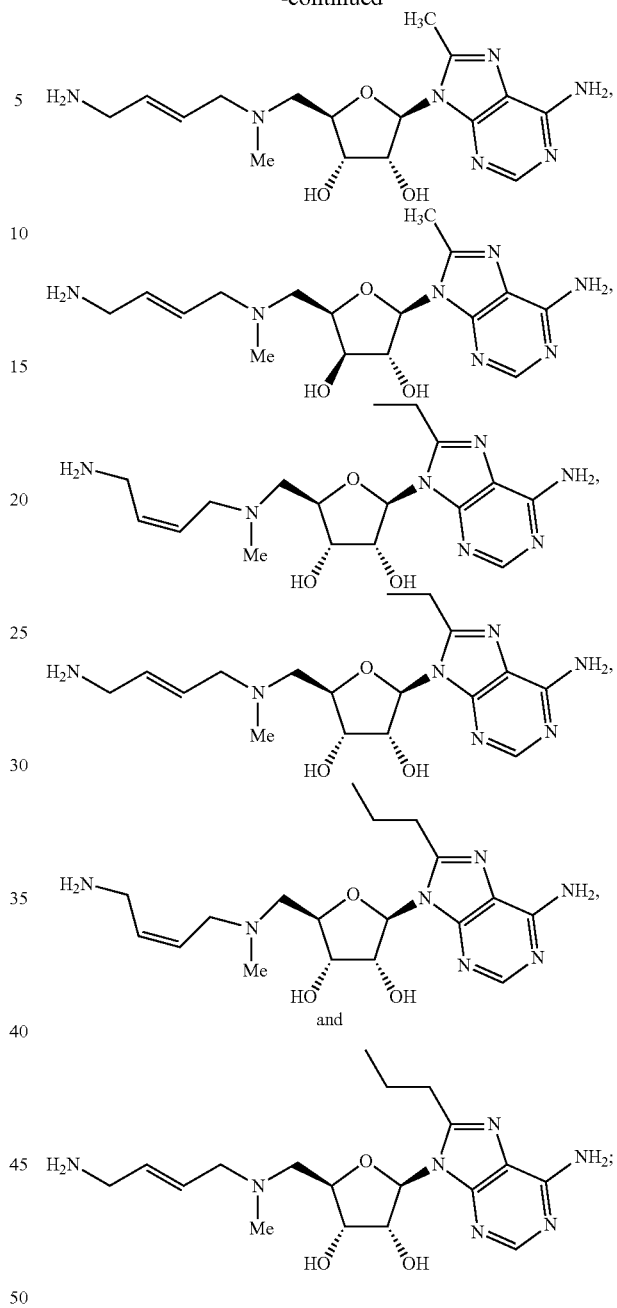

and pharmaceutically acceptable salts thereof.

13. A pharmaceutical composition comprising a compound according to claim 1, admixed with a pharmaceutically acceptable excipient.

14. The pharmaceutical composition of claim 13, further comprising an additional therapeutic agent selected from eflornithine (difluoromethyl ornithine), pentamidine, suramin, melarsoprol, and nifurtimox.

15. A method to treat a subject infected with an African trypanosome, said method comprising administering to the subject an effective amount of a compound according to claim 1.

16. The method of claim 15, further comprising administering to the subject an effective amount of an additional therapeutic agent selected from eflornithine (difluoromethyl ornithine), pentamidine, suramin, melarsoprol, and nifurtimox.

17. The compound of claim 1, wherein W is $CR^{10}$.

18. The compound of claim 1, wherein one of $R^8$ and $R^9$ is F.

* * * * *